US006784340B1

(12) United States Patent
Aoyama et al.

(10) Patent No.: US 6,784,340 B1
(45) Date of Patent: Aug. 31, 2004

(54) CHEMICAL INDUCIBLE PROMOTER USED TO OBTAIN TRANSGENIC PLANTS WITH A SILENT MARKER

(75) Inventors: Takashi Aoyama, Shiga (JP); Jianru Zuo, New York, NY (US); Nam-Hai Chua, Scarsdale, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/438,392

(22) Filed: Nov. 12, 1999

Related U.S. Application Data

(63) Continuation-in-part of application No. 09/014,592, filed on Jan. 28, 1998, now Pat. No. 6,063,985.
(51) Int. Cl.[7] .......................... A01H 1/00; C12N 15/82; C12N 15/00; C07H 21/02; C07H 21/04
(52) U.S. Cl. ....................... 800/290; 435/6; 435/91.1; 435/320.1; 435/468; 536/23.1; 536/23.6; 800/278; 800/295
(58) Field of Search ......................... 435/6, 91.1, 468, 435/69.7, 320.1; 536/23.1, 23.2, 23.6, 24.1, 24.2, 25.3; 800/278, 290, 295

(56) References Cited

U.S. PATENT DOCUMENTS

| 5,880,331 A | * | 3/1999 | Krebbers et al. | ............ 800/205 |
| 6,031,151 A | * | 2/2000 | Draper | ........................ 800/205 |
| 6,147,282 A | * | 11/2000 | Goff et al. | ................... 800/303 |

FOREIGN PATENT DOCUMENTS

| EP | 334 383 A3 | 9/1989 |
| EP | 334 383 A2 | 9/1989 |
| WO | WO 98/05754 A2 | 2/1998 |
| WO | WO 98/05754 A3 | 2/1998 |
| WO | WO 98/36637 A1 | 8/1998 |
| WO | WO 99/38988 A3 | 8/1999 |
| WO | WO 99/38988 A2 | 8/1999 |

OTHER PUBLICATIONS

Sylvia Braselmann et al., Proc. Natl. Sci. USA, vol. 90, pp. 1657–1661, Mar. 1993.*
Takashi Aoyama et al., The Plant Journal, (1997) 11 (3), pp. 606–612.*
Louvion et al. Gene, 1993, vol. 131, pp 129–134.*
Bruce, W. et al., "Expression Profiling of the Maize Flavonoid Pathway Genes Controlled by Estradiol–inducible Transcription Factors CRC and P," *The Plant Cell* (2000) 12:65–79.
Zuo J. et al., "An Estrogen Receptor–based Transactivator XVE Mediates Highly Inducible Gene Expression in Transgenic Plants," *The Plant Journal* (2000) 24(2), 265–273.
Akiyoshi, D.E. et al. "T–DNA of *Agrobacterium tumefaciens* encodes an enzyme of cytokinin biosynthesis", *Proc. Natl. Acad. Sci. USA*, Oct. 1984; 81:5994–5998.

Aoyama, T. and Chua, N.–H. "A glucocorticoid–mediated transcriptional induction system in transgenic plants", *Plant J.* (1997); 11:605–612.
Aoyama, T. et al. "Ectopic Expression of the Arabidopsis Transcriptional Activator Athb–1 Alters Leaf Cell Fate in Tobacco", *Plant Cell*, Nov. 1995; 7:1773–1785.
Aoyama T. "Glucocorticoid–inducible Gene Expression in Plants", *Inducible Gene Expression in Plants* (Ed. P. Reynolds), CAB International (Wallingford) (1999), pp. 43–59.
Barry, G.F. et al. "Identification of a cloned cytokinin biosynthetic gene", *Proc. Natl. Acad. Sci. USA*, Aug. 1984; 81:4776–4780.
Beato, M. "Gene Regulation by Steroid Hormones", *Cell*, Feb. 10, 1989; 56:335–344.
Becker, D. et al. "New plant binary vectors with selectable markers located proximal to the left T–DNA border" *Plant Molecular Biology* (1992); 20:1195–1197.
Benfey, P.N. and Chua, N.–H. "The Cauliflower Mosaic Virus 35S Promoter: Combinatorial Regulation of Transcription in Plants", *Science*, Nov. 16, 1990; 250:959–966.
Bevan, M.W. and Chilton M.–D. "T–DNA of the Agrobacterium T1 and RI Plasmids", *Ann. Rev. Genet.*, 1982; 16:357–384.
Boase, M.R. et al. Genetic Transformation Mediated by *Agrobacterium Tumefaciens* of Florists'Chrysanthemum (*Dendranthema Xgrandiflorum*) Cultivar 'Peach Margaret', In Vitro Cell. Dev. Biol.–Plant, Mar. 1998; 34:46–51.
Böhner, S. et al. "Transcriptional activator TGV mediates dexamethasone–inducible and tetracycline–inactivatable gene expression", *The Plant Journal* (1999); 19(1):87–95.
Braselmann, S. et al. "A selective transcriptional induction system for mammalian cells based on Ga14–estrogen receptor fusion proteins", *Proc. Natl. Acad. Sci. USA*, Mar. 1993; 90:1657–1661.
Chuck, G. et al. "KNAT1 Induces Lobed Leaves with Ectopic Meristems When Overexpressed in Arabidopsis", *The Plant Cell*, Aug. 1996; 8:1277–1289.

(List continued on next page.)

*Primary Examiner*—Ram R. Shukla
*Assistant Examiner*—Jane Zara
(74) *Attorney, Agent, or Firm*—Rothwell Figg Ernst & Manbeck

(57) ABSTRACT

A chemically inducible promoter is described that may be used to transform plants, including tobacco and lettuce, with genes which are easily regulatable by adding the plants or plant cells to a medium containing an inducer of the promoter or by removing the plants or plant cells from such medium. The promoter described is one that is inducible by a glucocorticoid which is not endogenous to plants. Such promoters may be used with a variety of genes such as ipt or knotted1 to induce shoot formation in the presence of a glucocorticoid. The promoter may also be used with antibiotic or herbicide resistance genes which are then regulatable by the presence or absence of inducer rather than being constitutive. Other examples of genes which may be placed under the control of the inducible promoter are also presented.

15 Claims, 16 Drawing Sheets

OTHER PUBLICATIONS

Coruzzi, G. et al. "Tissue–specific and light–regulated expression of a pea nuclear gene encoding the small subunit of ribulose–1,5–bisphosphate carboxylase", *The EMBO Journal*, 1984; 3(8):1671–1679.

Dalrymple, M.A. et al. "DNA sequence of the herpes simplex virus type 1 gene whose product is responsible for transcriptional activation of immediate early promoters", *Nucleic Acids Research*, 1985; 13(21):7865–7879.

De Veylder, L. et al. "Herbicide Safener–Inducible Gene Expression in *Arabidopsis thaliana*", *Plant Cell Physiol.*, 1997; 38(5):568–577.

Ebinuma, H. et al. "Selection of marker–free transgenic plants using the isopentenyl transferase gene", *Proc. Natl. Acad. Sci. USA*, Mar. 1997; 94:2117–2121 + cover page.

Faiss, M. et al. "Conditional transgenic expression of the *ipt* gene indicates a function for cytokinins in paracrine signaling in whole tobacco plants", *The Plant Journal*, 1997; 12(2):401–415.

Gan, S. and Amasino, R.M. "Inhibition of Leaf Senescence by Autoregulated Production of Cytokinin", *Science*, Dec. 22, 1995; 270:1986–1988.

Gatz, C. "Chemically inducible promoters in transgenic plants", *Curr. Opin. Biotechnol.*, 1996; 7:168–172.

Gatz, C. et al. "Stringent repression and homogeneous de–repression by tetracycline of a modified CaMV 35S promoter in intact transgenic tobacco plants", *The Plant Journal*, 1992; 2(3):397–404.

Gatz, C. "Chemical Control of Gene Expression", *Annu. Rev. Plant Physiol. Plant Mol. Biol.*, 1997; 48:89–108.

Gatz, C. and Lenk, I. "Promoters that respond to chemical inducers", *Trends Plant Sci.*, Sep. 1998; 3(9):352–358.

Giniger, E. et al. "Specific DNA Binding of GAL4, A Positive Regulatory Protein of Yeast", *Cell*, Apr. 1985; 40:767–774.

Goodrich, J.A. et al. "Drosophila TAF 40 Interacts with Both a VP16 Activation Domain and the Basal Transcription Factor TFIIB", *Cell*, Nov. 5, 1993; 75:519–530.

Greene, G.L. et al. "Sequence and Expression of Human Estrogen Receptor Complementary DNA", *Science*, Mar. 1986; 231:1150–1154.

Harms, C.T. et al. "Herbicide resistance due to amplification of a mutant acetohydroxyacid synthase gene", *Mol. Gen. Genet.*, 1992; 233:427–435.

Hattori, J. et al. "Multiple resistance to sulfonylureas and imidazolinones conferred by an acetohydroxyacid synthase gene with separate mutations for selective resistance", *Mol. Gen. Genet.*, 1992; 232:167–173.

Hattori, J. et al. "An acetohydroxy acid synthase mutant reveals a single site involved in multiple herbicide resistance", *Mol. Gen. Genet.*, 1995; 246:419–425.

Horii, T. et al. "Nucleotide Sequence of the *lexA* Gene of E. coli", *Cell*, Mar. 1981;23:689–697.

Ishige, F. et al. "A G–box motif (GCCACGTGCC) tetramer confers high–level constitutive expression in dicot and monocot plants", *The Plant Journal*, 1999; 18(4):443–448.

Kakimoto, T. "CKI1, a Histidine Kinase Homolog Implicated in Cytokinin Signal Transduction", *Science*, Nov. 8, 1996; 274:982–985.

Kang, H–G et al. "A glucocorticoid–inducible transcription system causes severe growth defects in *Arabidopsis* and induces defense–related genes", *The Plant Journal*, 1999; 20(1):127–133.

Keegan, L. et al. "Separation of DNA Binding from the Transcription–Activating Function of a Eukaryotic Regulatory Protein", *Science*, Feb. 1986, 231:699–704.

Klee, H. et al. "*Agrobacterium*–Mediated Plant Transformation and its Further Applications to Plant Biology", *Ann. Rev. Plant Physiol.*, 1987; 38:467–486.

Klee, H. et al. "E2. Transgenic Plants in Hormone Biology", in *Plants Hormones* (ed. P.J. Davies) (Kluwer Academic Publishers (Netherlands)) (1995), pp. 340–353.

Kost, B. et al. "A GFP–mouse talin fusion protein labels plant actin filaments in vivo and visualizes the actin cytoskeleton in growing pollen tubes", *The Plant Journal*, 1998; 16(3):393–401.

Kunkel, T. et al. "Inducible isopentenyl transferase as a high–efficiency marker for plant transformation", *Nature Biotechnology*, Sep. 1999; 17:916–919.

Laughon, A. et al. "Primary Structure of the *Saccharomyces cerevisiae GAL4 Gene*", *Mol. Cell. Biol.*, Feb. 1984; 4:260–267.

Li, Y. et al. "Altered Morphology in Transgenic Tobacco Plants That Overproduce Cytokinins in Specific Tissues and Organs", *Developmental Biology*, 1992; 153:386–395.

Lin, Y–S et al. "Binding of general transcription factor TFIIB to an acidic activating region", *Nature*, Oct. 10, 1991; 353:569–571.

Lincoln, C. et al. "A *knotted1*–like Homeobox Gene in Arabidopsis is Expressed in the Vegetative Meristem and Dramatically Alters Leaf Morphology When Overexpressed in Transgenic Plants", *The Plant Cell*, Dec. 1994; 6:1859–1876.

Lloyd, A.M. et al. "Epidermal Cell Fate Determination in *Arabidopsis*: Patterns Defined by a Steroid–Inducible Regulator", *Science*, Oct. 21, 1994; 266:436–439.

Louvion, J–F et al. "Fusion of GAL4–VP16 to a steroid–binding domain provides a tool for gratuitous induction of galactose–responsive genes in yeast", *Gene*, 1993; 131:129–134.

Lyon, B.R. et al. "Cotton plants transformed with a bacterial degradation gene are protected from accidental spray drift damage by the herbicide 2,4–dichlorophenoxyacetic acid", *Transgenic Research*, 1993; 2:162–169.

Lyon, B.R. et al. "Expression of a bacterial gene in transgenic tobacco plants confers resistance to the herbicide 2,4–dichlorophenocyacetic acid", *Plant Molecular Biology*, 1989; 13:533–540.

Martinez, A. et al. "Ecdysone agonist inducible transcription in transgenic tobacco plants", *The Plant Journal*, 1999; 19(1):97–106.

McKenzie, M.J. et al. "Controlled Cytokinin Production in Transgenic Tobacco Using a Copper–Inducible Promoter", *Plant Physiol.*, 1998; 116:969–977.

McNellis. T.W. et al. "Glucocorticoid–inducible expression of a bacterial avirulence gene in transgenic *Arabidopsis* induces hypersensitive cell death", *The Plant Journal*, 1998; 14(2):247–257.

Medford, J.I. et al. "Alterations of Endogenous Cytokinis in Transgenic Plants Using a Chimeric Isopentenyl Transferase Gene", *The Plant Cell*, Apr. 1989; 1:403–413.

Miesfeld, R. et al. "Genetic Complemetation of a Glucocorticoid Receptor Deficiency by Expression of Cloned Receptor cDNA", *Cell*, Aug. 1, 1986; 46:389–399.

Miki, T. et al. "Organization of the *lexA* gene of *Escherichia coli* and nucleotide sequence of the regulatory region", *Nucleic Acids Research*, 1981; 9(3):529–543.

Millar, A.J. et al. "A Novel Circadian Phenotype Based on Firefly Luciferase Expression in Transgenic Plants", *The Plant Cell*, Sep. 1992; 4:1075–1087.

Morris, R.O. "E. Molecular Aspects of Hormone Synthesis and Action. E1. Genes Specifying Auxin and Cytokinin Biosynthesis in Prokaryotes", in *Plant Hormones* (ed. P.J. Davies) (1995) (Kluwer Academic Publishers (Netherlands)), pp. 318–339.

Napoli, C. et al. "Introduction of a Chimeric Chalcone Synthase Gene into Petunia Results in Reversible Co–Suppression of Homologous Genes *in trans*", *The Plant Cell*, Apr. 1990; 2:279–289.

Odell, J.T. et al. "Identification of DNA sequences required for activity of the cauliflower mosaic virus 35S promoter", *Nature*, Feb. 1985; 313:810–812.

Picard, D. et al. "A Movable and Regulable Inactivation Function within the Steroid Binding Domain of the Glucocorticoid Receptor", *Cell*, Sep. 23, 1988; 54:1073–1080.

Picard, D. "Steroid–binding domains for regulating the functions of heterologous proteins *in cis*", *Trends in Cell Biology*, Aug. 1993; 3:278–280.

Rathore, K.S. et al. "Use of *bar* as a selectable marker gene and for the production of herbicide–resistant rice plants from protoplasts" *Plant Molecular Biology*, 1993; 21:871–884.

Redig, P. et al. "Analysis of Cytokinin Metabolism in *ipt* Transgenic Tobacco by Liquid Chromatography–Tandem Mass Spectrometry", *Plant Physiol.*, 1996; 112:141–148.

Rusconi, S. et al. "Functional dissection of the hormone and DNA binding activities of the glucocorticoid receptor", *The EMBO Journal*, 1987; 6(5):1309–1315.

Sadowski, I. et al. "GAL4–VP16 is an unusually potent transcriptional activator", *Nature*, Oct. 6, 1988; 335:563–564.

Schena, M. et al. "A steroid–inducible gene expression system for plant cells", *Proc. Natl. Acad. Sci. USA*, Dec. 1991; 88:10421–10425.

Shinmyo, A. et al. "Construction of Gene Expression System in Cultured Tobacco Cells", *Ann. N.Y. Acad. Sci.*, 1996; 782:97–106.

Smigocki, A.C. et al. "Cytokinin gene fused with a strong promoter enhances shoot organogenesis and zeatin levels in transformed plant cells", *Proc. Natl. Acad. Sci. USA*, Jul. 1988; 85:5131–5135.

Smigocki, A.C. et al. "Cytokinin–to–Auxin Ratios and Morphology of Shoots and Tissues Transformed by a Chimeric Isopentenyl Transferase Gene", *Plant Physiol.*, 1989; 91:808–811.

Smigocki, A.C. "Cytokinin content and tissue distribution in plants transformed by a reconstructed isopentenyl transferase gene", *Plant Molecular Biology*, 1991; 16:105–115.

Smigocki, A. et al. "Cytokinin–mediated insect resistance in *Nicotiana* plants transformed with the *ipt* gene", *Plant Molecular Biology*, 1993; 23:325–335.

Tamaoki, M. et al. "Ectopic Expression of a Tobacco Homeobox Gene, NTH15, Dramatically Alters Leaf Morphology and Hormone Levels in Transgenic Tobacco", *Plant Cell Physiol*, 1997; 38:917–927.

Thomas, J.C. et al. "Light–induced expression of *ipt* from *Agrobacterium tumefaciens* results in cytokinin accumulation and osmotic stress symptoms in transgenic tobacco", *Plant Molecular Biology*, 1995; 27:225–235 + *Plant Molecular Biology*, 1995; 28:965 Erratum.

Tran Thanh Van, K.M. "Control of Morphogenesis in in vitro Cultures", *Ann. Rev. Plant Physiol.*, 1981; 32:291–311.

Triezenberg. S.J. et al. "Functional dissection of VP16, the trans–activation of herpes simples virus immediate early gene expression", *Gene & Development*; 1988; 2:718–729.

Waldron, C. et al. "Resistance to hygromycin B", *Plant Molecular Biology*; 1985; 5:103–108.

Wiersma, P.A. et al. "Isolation, expression and phylogenetic inheritance of an acetolactate synthase gene from *Brassica napus*", *Mol. Gen. Genet.*, 1989; 219:413–420.

Ooms. G. et al. "From tumour to tuber; tumour cell characteristics and chromosome numbers of crown gall–derived tetraploid potato plants (*Solanum tuberosum* cv. 'Maris Bard')", *Theor. Appl. Genet.*, 1983; 66:169–172.

\* cited by examiner (A) Tobacco  (B) Lettuce
Fig. 9A   Fig. 9B
Fig. 9C  Fig. 9D
Fig. 9E   Fig. 9F LB– G10-90 –GVG–E9–NOS–Hpt–NOS 3'–

———6xUAS–Ipt–3A–35S–Luc–CaMV 3'–RB

Fig. 12

CHEMICAL INDUCIBLE PROMOTER USED TO OBTAIN TRANSGENIC PLANTS WITH A SILENT MARKER

CROSS REFERENCE TO RELATED APPLICATIONS

This is a continuation in part of Ser. No. 09/014,592, filed Jan. 28, 1998, now U.S. Pat. No. 6,063,985 which is incorporated herein by reference.

STATEMENT REGARDING FEDERALLY SPONSORED RESEARCH

This application was made in part with Government support under DOE Grant #FG02-94ER20142, funded by the Department of Energy.

BACKGROUND OF THE INVENTION

Transgenic techniques have become a powerful tool for addressing important biological problems in multicellular organisms, and this is particularly true in the plant field. Many approaches that were impossible to implement by traditional genetics can now be realized by transgenic techniques, including the introduction of homologous or heterologous genes into plants, with modified functions and altered expression patterns. The success of such techniques often depends upon the use of markers to identify the transgenic plants and promoters to control the expression of the transgenes.

Selectable markers are widely used in plant transformation. Historically such markers have often been dominant genes encoding either antibiotic or herbicide resistance (Yoder and Goldsbrough, 1994). Such markers include the antibiotic resistance markers nptII, Ble, cat, aphIV, SPT, aacC3 and aacC4, the herbicide resistance markers bar, EPSP, bxn, psbA, tfdA, sul and csr1-1, and the selectable markers dhfr, DHPS, AK and tdc. Although such markers are highly useful, they do have some drawbacks. The antibiotics and herbicides used to select for the transformed cells generally have negative effects on proliferation and differentiation and may retard differentiation of adventitious shoots during the transformation process (Ebinuma et al., 1997). Also, some plant species are insensitive to or tolerant of these selective agents, and therefore, it is difficult to separate the transformed and untransformed cells or tissues (Ebinuma et al., 1997). Further, these genes are constitutively expressed, and there are environmental and health concerns over inserting such constitutively expressed genes in plants which are grown outside of a laboratory setting (Bryant and Leather, 1992; Gressel, 1992; Flavell et al., 1992).

One marker that is neither an antibiotic nor a herbicide is the ipt gene from the Ti-plasmid of *Agrobacterium tumefaciens*. This gene encodes isopentenyltransferase, which is used in cytokinin synthesis (Barry et al., 1984). Isopentenyltransferase uses 5'-AMP and isopentenyl diphosphate to catalyze the formation of isopentenyl-adenosine-5'-monophosphate, the first intermediate in cytokinin biosynthesis. Overexpression of the ipt gene leads to elevated cytokinin levels (Medford et al., 1989; McKenzie et al., 1998; Faiss et al., 1997; Redig et al., 1996; Ebinuma et al., 1997). Cytokinins are plant hormones that play an important role in plant development by mediating a range of morphological changes (Mok and Mok, 1994; Davies, 1995; Coenen and Lomax, 1997). For example, cytokinins are able to stimulate leaf expansion and delay leaf senescence (Kuraish and Okumura, 1956; Wingler et al., 1998; Gan and Amasino, 1995). In young, dark-grown seedlings, high cytokinin levels can produce a deetiolated phenotype, resembling the morphology of light-grown seedlings with short hypocotyls, open hooks and expanded cotyledons (Chaudhury et al., 1993; Miklashevichs and Walden, 1997). Cytokinins can also release lateral buds from apical dominance, and stimulate de novo bud formation (Cline, 1991; Skoog and Miller, 1957; Sachs and Thimmann, 1967). This class of hormones thus plays a critical role in the formation of adventitious shoots. As demonstrated by Skoog and Miller (1957), high cytokinin levels can induce shoot differentiation from tobacco calli, a prerequisite for the regeneration of transgenic plants. Besides supporting tumor growth, T-DNA introduction into a plant cell can also induce regeneration of physiologically abnormal shoots from transformed protoplasts or leaf discs.

Overexpression of the ipt gene (Akiyoshi et al., 1984; Barry et al., 1984), a component of the T-DNA, leads to increased cytokinin relative to auxin, which triggers shoot regeneration (Tran Thanh Van, 1981). This overproduction of shoots can result in a phenotype of a large number of shoots (hereafter "shooty phenotype"). This phenotype can be used as a marker (Ebinuma et al., 1997). Studies using the ipt gene under the control of constitutive promoters showed that ipt overexpression causes elevated cytokinin levels in transgenic plants (Smigocki and Owens, 1988; Medford et al., 1989). A chimeric ipt gene under the control of the cauliflower mosaic virus (CaMV) promoter has been introduced into cells of potato (Ooms et al., 1983), cucumber (Smigocki and Owens, 1989), and several Nicotiana species (Smigocki and Owens, 1988) and these transgenic cells proliferated and exhibited an extreme shooty phenotype and loss of apical dominance in hormone-free medium. Studies have shown that in plants transformed with ipt to overproduce cytokinins, the cytokinins work only locally as a paracrine hormone (Faiss et al., 1997). Grafting experiments performed with wild type tobacco plants and tobacco plants in which the ipt gene was overexpressed showed that the increased cytokinin levels remained restricted to the part of the plant that overexpressed ipt (Faiss et al., 1997).

One problem with the use of constitutively expressed ipt as a marker is that the resulting transgenic plants lose apical dominance and are unable to root due to overproduction of cytokinins (Ebinuma et al., 1997). In addition, plants which constitutively overexpress ipt possess an altered leaf morphology and delayed leaf senescence. Such plants show little root growth and poor internode elongation, display delayed leaf senescence, and are very often sterile (Mok and Mok, 1994; Klee et al., 1987; Ebinuma et al., 1997).

Ebinuma et al. (1997) developed one method to use the ipt marker to overcome the problems associated with constitutive overexpression of ipt. They developed a vector in which the ipt gene was inserted into a plasmid which included the transposable element Ac. The construct included the T-DNA (portion of the Ti plasmid that is transferred to plant cells) and the 35S CaMV promoter. This construct was transformed into *A. tumefaciens*. Leaf segments were inoculated with the transformed bacteria and grown on nonselective media. In rare cases, the Ac-element failed to re-integrate or integrated into a sister chromatid after its excision. Abnormal shoots with an extra shooty phenotype were selected and cultivated further for six months. From these, several normal shoots grew. Some of these were a result of the transposable element Ac having excised from the genome along with the ipt gene, as determined by DNA analysis.

Some of these plants retained the other necessary markers which had also been included in the plasmid. This method therefore overcomes the problems of having a constitutively expressed ipt gene present. Unfortunately, this method requires many months of cultivation and results in only a few plants that have lost the ipt gene. Ebinuma et al. (1997) report that 6 months after infection the frequency of marker free plants was 0.032%. Furthermore, the selection of "normal" shoots from abnormal regenerants was based on a variable morphological criterion. The morphological selection also does not distinguish between plants that lost the 35S-ipt gene and chimeric plants or plants with very low ipt expression level.

The use of inducible promoters is another means that has been used to overcome the problems associated with the constitutive overexpression of the ipt gene in transgenic plants. The use of a copper-inducible promoter to regulate ipt expression led to the specific expression of the ipt gene in the roots, the major organ for cytokinin biosynthesis (McKenzie et al., 1998). In addition, regulated ipt expression by the tetracycline inducible system (Gatz et al., 1992) provided data about the biological effects of cytokinins in plants and their transport through the vascular system (Faiss et al., 1997; Redig et al., 1996). Transgenic plants carrying the ipt gene under the control of heat shock (Medford et al., 1989) and light inducible promoters (Redig et al., 1996) have also been reported. All of these systems were used to study the biological effects of cytokinins and were not used for transformation.

The CKI1 gene was recently identified (Kakimoto, 1996). Overproduction of this gene in plants results in plants that exhibit typical cytokinin responses, including rapid cell division and shoot formation in tissue culture in the absence of exogenous cytokinin (Kakimoto, 1996). The CKI1 gene can be used as a selectable marker in a manner similar to ipt, i.e., the CKI1 gene can be put under the control of a promoter and overexpressed in transgenic plant cells thereby inducing shoot formation in the absence of exogenous plant hormones. Such shoots can be excised, thereby obtaining transgenic plants. Such shoots, obtained either from cells transformed with ipt or CKI1, cannot be made to grow normally while the cells overexpress these transgenes.

The knotted gene and knotted-like genes are a third group of genes which when overexpressed can lead to ectopic production of adventitious shoots (Chuck et al., 1996; Lincoln et al., 1994). These genes include kn1 of maize, KNAT1, KNAT2, kn1-like genes of maize, kn1-like gene of rice and kn1-like gene of soybean. These genes can be used as selectable markers in the same manner as the ipt and CKI1 genes.

In addition to the use of markers to identify transgenic plants, the use of promoters to control expression of the transgenes is a normal part of such experiments. In most experiments, the transgenes are transcribed from a strong promoter, such as the 35S promoter of the cauliflower mosaic virus (CaMV). However, a more flexible gene expression system is needed to extract greater benefits from transgenic technology. Good inducible transcription systems are desired because transgenic plants with inducible phenotypes are as useful as conditional mutants isolated by traditional genetics. In this regard, several induction systems have been reported and successfully used (Ainley and Key, 1990; Gatz et al., 1992; Mett et al., 1993; Weinmann et al., 1994). Among these, the tetracycline-dependent expression systems are the most advanced (for review, see Gatz, 1996).

The glucocorticoid receptor (GR) is a member of the family of animal steroid hormone receptors. GR is not only a receptor molecule but also a transcription factor which, in the presence of a glucocorticoid, activates transcription from promoters containing glucocorticoid response elements (GREs) (for reviews, see Beato, 1989; Picard, 1993). It has been thought that the GR system could be a good induction system in plants because it is simple, and glucocorticoid itself does not cause any pleiotropic effects in plants. Nevertheless, a general and efficient glucocorticoid-inducible system using GR has not previously been constructed for transgenic plants, although it has been demonstrated that a system comprising GR and GREs could work in a transient expression system with cultured plant cells (Schena et al., 1991). On the other hand, it has been reported that the (hormonal) regulatory region (or domains) of GR could regulate the function of plant transcription factors in transgenic plants (Aoyama et al., 1995; Lloyd et al., 1994). Lloyd et al. (1994) showed that trichome development in Arabidopsis could be successfully controlled by a chimeric protein comprising the glucocorticoid regulatory domains and the maize transcriptional regulator R. However, the construction of such a chimeric transcription factor whose activity is tightly regulated by the glucocorticoid receptor domain is not always easy and achievable in every case. Tight regulation appears to be critically dependent on the intramolecular structure of the chimeric protein, especially the relative position between the glucocorticoid receptor domain and the domain whose function is to be regulated.

The regulatory region of animal steroid hormone receptors, which include a hormone binding domain (HBD) and binding sites for HSP90, are thought to have repressive effects on covalently linked, neighboring domains in the absence of their cognate ligands, and binding of the appropriate ligand to an HBD results in de-repression (Picard, 1993). This mechanism was taken advantage of by designing a transcription factor in which a constitutively active transactivating function was regulated by the regulatory region of the rat GR in cis (Picard et al., 1988; Rusconi and Yamamoto, 1987). A chimeric transcription factor comprising the DNA-binding domain of the yeast transcription factor GAL4 (Keegan et al., 1986) and the transactivating domain of the herpes viral protein VP16 (Triezenberg et al., 1988) was chosen as a constitutively active transactivating function. The chimeric protein GAL4-VP16 was thought to act as a strong transcription factor in all cell types because the activation domain of VP16 is known to interact directly with general transcription factors, which are thought to be evolutionarily conserved among eukaryotes (Goodrich et al., 1993; Lin et al., 1991; Sadowski et al., 1988). It has been shown that the regulatory region of the human estrogen receptor could regulate similar chimeric transcription factors in yeast and animal tissue culture cells (Braselmann et al., 1993; Louvion et al., 1993). The regulatory region of the rat GR was added to the chimeric transcription factor and the resulting hybrid transcription factor was designated 'GVG' because it consists of one domain each from GAL4, VP16 and GR. A DNA fragment encoding the GVG transcription factor was placed between the cauliflower mosaic virus 35S promoter (Odell et al., 1985) and the poly(A) addition sequence of the pea ribulose bisphosphate carboxylase small subunit rbcS-E9 (Coruzzi et al., 1984). As a binding site for GVG, a DNA fragment containing six copies of the GAL4 UAS (Giniger et al., 1985) was fused 5' to the minimal CaMV 35S promoter (−46 to +9).

The publications and other materials used herein to illuminate the background of the invention, and in particular cases to provide additional details respecting the practice, are incorporated herein by reference, and for convenience, are referenced by author and date in the text and respectively grouped in the appended List of References.

SUMMARY OF THE INVENTION

Overexpression of the isopentenyl transferase gene (ipt) from the Ti-plasmid of *Agrobacterium tumefaciens* can increase the endogenous level of cytokinin in transgenic plants leading to the regeneration of shoots from transformed plant cells. When combined with a dexamethasone (DEX) inducible system the controlled expression of the ipt gene can be used to specifically select for transgenic regenerants without the need for an antibiotic-resistance marker. The combined system allows high efficiency co-transformation with additional genes and produces transgenic plants without morphological or developmental defects.

The invention relates in one aspect to a method for selecting transgenic plants using a selectable marker that is under the control of a chemically inducible promoter. The method involves the steps of transforming a plant cell with a vector containing an ipt gene, CKI1 gene or a gene from the knotted family, under the control of a chemically inducible promoter; growing the plant cells in the absence of plant hormone but in the presence of an inducer of the promoter; and excising the shoots that develop. The invention further relates to a method for selecting transgenic tobacco and transgenic lettuce plants using a selectable marker that is under the control of a chemically inducible promoter.

In another aspect, the invention relates to a vector that is useful for making transgenic plants. The vector is designed such that it includes a selectable marker that is under the control of a promoter that is chemically inducible rather than constitutive.

The invention further relates to methods of using the above described inducible vector.

The invention relates in another aspect to a transgenic plant or transgenic plant cell containing a vector with a selectable marker that is under the control of a chemically inducible promoter. In one aspect of the invention the transgenic plants are tobacco or lettuce plants and the transgenic plant cells are tobacco or lettuce cells.

The invention relates in another aspect to a method for selecting transgenic plants using antibiotic and herbicide resistance genes that are under the control of a chemically inducible promoter. Such antibiotic and herbicide resistance genes can be regulated by the presence or absence of inducer.

The invention relates in another aspect to a transgenic plant containing a herbicide resistance gene or an antibiotic resistance gene that is under the control of a chemically inducible its promoter. The invention further relates to a transgenic tobacco plant or transgenic lettuce plant containing a herbicide resistance gene that is under the control of a chemically inducible promoter.

The invention also relates to a method of selecting root cells transformed with ipt, CKI1 or knotted in the presence of low levels of auxins and cytokinins.

BRIEF DESCRIPTION OF THE DRAWINGS

FIG. 4A is a color scale showing luminescence intensity from dark gray (lowest) to white (highest) (as in FIG. 3, the luminescence is blue, not gray as shown in the figure). FIG. 4B represents a transgenic plant grown in a pot for 3 weeks and then sprayed with a solution containing 0.5 mM potassium luciferin and 0.01% (w/v) Tween-20 and assayed for luciferase activity. FIG. 4C represents the same plant as in FIG. 4B but here the plant was then sprayed with a solution containing 30 μM DEX and 0.01% (w/v) Tween-20. Twenty-four hours later, the plant was sprayed again with the luciferin solution and assayed. For both FIGS. 4B and 4C, the luminescence from the plant was imaged using a high-sensitivity camera system (Hamamatsu Photonic Systems). Heterogeneity of the luminescence seen in the plant treated with DEX was caused by uneven absorption of luciferin.

FIGS. 9A–F show luciferase activity in tobacco and lettuce regenerants. Luciferase activities were measured in 40 day-old regenerants grown under inductive conditions (10 µM DEX) for expression of the ipt gene. Luciferase activity in regenerants was measured using a video imaging system with measurements integrated over 5 minutes and subtraction of background from the images. The luciferase images were transformed from 16 to 8 bit pictures and artificially colored for presentation. The red/green overlay shows a superimposition of the bright-field and luciferase activity images to allow easy detection of luc positive and negative regenerants. FIGS. 9A, 9C and 9E are tobacco and FIGS. 9B, 9D and 9F are lettuce. FIGS. 9A–B show bright-field pictures, 9C–D are luciferase images and 9E–F are with a red/green overlay.

FIGS. 10A and 10C show ipt transcript levels and FIGS. 10B and 10D show luc transcript levels.

FIG. 12 shows the transformation cassette for inducible expression of the ipt gene. The ipt gene from *Agrobacterium tumefaciens* was cloned under the control of a glucocorticoid-responsive promoter (6×UAS fused to −46 of the CaMV 35S minimal promoter) to allow regulated expression of the gene. Expression of the ipt gene is mediated by a glucocorticoid-activated transcription factor (GVG) as described by Aoyama and Chua (1997). The genes encoding hygromycin phosphotransferase (hpt) (Waldron et al., 1985) and firefly luciferase (luc) (Millar et al., 1992) were cloned under the control of constitutive promoters (NP, NOS promoter; 35S; CaMV 35S promoter) to allow easy detection of transformation and co-transformation efficiencies. The above genes were cloned between the left and right border (LB, RB) of the T-DNA (Klee et al., 1987; Beavan and Chilton, 1982) (pBI 101, Clontech, Inc.) from the Ti plasmid of *Agrobacterium tumefaciens* to allow Agrobacterium-mediated transformation.

FIG. 14A shows roots of a pER8-GFP transgenic Arabidopsis line. The GFP signals (green) emitted from the same roots were viewed under a fluorescence microscope as shown in FIG. 14B.

DETAILED DESCRIPTION OF THE INVENTION

Figure 1:
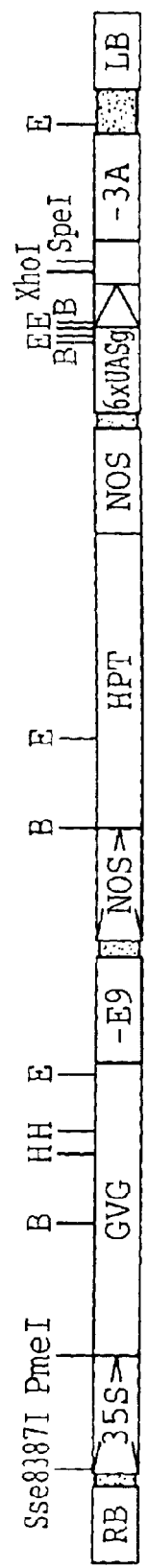
FIG. 1 is a schematic representation of the insert between the left and right borders in pTA7002. RB represents the right border and LB represents the left border. Restriction enzyme sites are shown above the drawing. The restriction enzyme sites represented by abbreviations are: B—BamHI, H—HindIII, E—EcoRI.

We reasoned that inducible systems can enable the development of protocols using the ipt gene as a transformation marker without the drawbacks of constitutive expression. Under inductive conditions, cells transformed with the ipt gene should have elevated cytokinin levels and hence the potential to regenerate shoots from plant calli or explants. In this context, the overexpression of the ipt gene can serve as an antibiotic-free marker system that specifically selects for transformed cells. As described by Aoyama and Chua (1997), the dexamethasone inducible system allows tightly regulated expression of target genes in transgenic plants. This system consists of a hybrid transcription factor that mediates transcription when activated with DEX and a regulated gene under the control of cis elements that respond only to this transcription factor. Hence, we used a transformation cassette containing the ipt gene under the control of the DEX-inducible system acting as an antibiotic-free marker for the co-transformation of two other constitutively expressed genes (hygromycin phosphotransferase (hpt)) (Waldron et al., 1985) and firefly luciferase (luc) (Millar et al., 1992). This new transformation system was established for both tobacco and lettuce using Agrobacterium-mediated transformation.

The present invention relates in one embodiment to transgenic plants that have been transformed with a vector that includes a selectable marker which is under the control of an inducible promoter. In a preferred embodiment of the invention the transgenic plant is a tobacco plant. In an alternate preferred embodiment of the invention the transgenic plant is a lettuce plant.

In one embodiment of the invention the vector that is used to form the transgenic plants includes a chemically inducible promoter that activates the selectable marker. If desired, any other gene of interest can also be put under control of the inducible promoter such that the gene can be turned on whenever desired. Such a gene need not be a marker. Examples of such vectors are presented in the following Examples which describe not only the vectors, but the methods used to prepare and screen for transgenic plants containing such vectors.

In one embodiment of the invention the promoter can be induced in order to select for cells or plants that have become transgenic but will not be induced under natural growth conditions. In this manner the selectable marker gene, although present in the transgenic plants, will be completely silent during the normal growth of the plants and should not interfere with the growth of the plants. Such a silent marker gene will also be more environmentally sound than, e.g., having an antibiotic resistance gene marker present wherein said resistance gene is expressed during the normal growth of the plant. The use of this latter type of marker is of concern because it may lead to the development of organisms resistant to the antibiotic.

In one embodiment of the invention the inducible promoter is the glucocorticoid receptor. This has been thought to be a good induction system for plants because glucocorticoid itself does not cause any pleiotropic effects in plants. In a preferred embodiment of the invention the transcription factor that binds the glucocorticoid receptor is a chimeric transcription factor in which the regulatory region of the rat GR is added to the DNA-binding domain of the yeast transcription factor GAL4 and the transactivating domain of the herpes viral protein VP16. The resulting hybrid transcription factor is designated 'GVG' because it consists of one domain each from GAL4, VP16 and GR. The GVG gene was introduced into tobacco together with a luciferase (Luc) reporter gene transcribed from a promoter containing six copies of the GAL4 upstream activating sequence (GAL4 UAS). Good induction of both the luciferase activity and the luc mRNA levels were observed upon glucocorticoid treatment.

A major advantage of the GVG system in plants is the fact that GR and glucocorticoid, at least at the concentrations used, are nontoxic and have no observable adverse physiological effects on plants, thus allowing the induction of target genes without pleiotropic effects. To retain this advantage, all the other components in the GVG system were also obtained from non-plant sources.

A further advantage of the system is that glucocorticoid possesses characteristics that make it suitable as an inducer chemical. Because glucocorticoid can easily permeate plant cells, rapid gene induction can be performed using various methods. A local induction of gene expression can be obtained simply by spraying with a glucocorticoid solution. It is clear that inducer chemicals accumulate in leaves to a high concentration when whole plants are treated under open air conditions. Even under such conditions, the accumulated glucocorticoid does not cause any visible damage to leaves. The induction level can be regulated by using different concentrations or different derivatives of glucocorticoid. This feature can be helpful for analyzing dose-dependent effects of induced gene products. Glucocorticoid is one of the best-studied biological compounds and over 100 different types of glucocorticoid derivatives are now available from commercial sources. Some of the glucocorticoid derivatives may be very stable in plants whereas others are rapidly degraded. These types of glucocorticoid would be useful for stable and transient induction, respectively. Moreover, some glucocorticoid antagonists might be used for down-regulation of induction.

Although specific constructs are described below, others may be easily envisioned and produced by one of skill in the art. The GVG system developed here is very flexible in its composition. For example, the transcriptional induction can be limited to a specific tissue by replacing the 35S promoter for the GVG gene with a tissue-specific promoter. Each functional domain in the GVG fusion protein is also exchangeable, allowing further refinement of the system. With a different DNA-binding domain and the regulatory region of another steroid hormone receptor, it is possible to develop another steroid induction system that can be used in combination with the GVG system.

Another construct has also been developed which has advantages over or in conjunction with the GVG system. This construct is referred to as XVE. It is similar to the GVG system but contains the DNA binding domain of the bacterial repressor LexA and the regulatory region of human estrogen receptor. The XVE construct can be used in place of the GVG construct wherever the GVG construct is described throughout this disclosure so long as the proper inducer is used for the construct being used. The XVE construct can be used together with the GVG construct and can be controlled separately from the GVG construct.

In a preferred embodiment of the invention the selectable marker utilized is the ipt gene. When this gene is induced it results in the extreme shooty phenotype in which plant cells grow many shoots rather than roots. This phenotype is easily selected by visual inspection. Once the inducing agent is removed, the ipt gene becomes silent and the cells are able to grow normally. In other embodiments of the invention other selectable markers, e.g., the CKI1 gene may be used in a similar fashion. Again, whatever marker is used will be active only while induced and will be silent once the chemical inducer is removed.

A variety of DNA constructs can be made that incorporate the principle of using a chemical inducible marker. The theory behind the design of the plasmids, which are described in detail below, was to assemble regions within a plasmid which could be well controlled.

Another embodiment of the invention relates to a method for selecting transgenic plants using a selectable marker that is under the control of a chemically inducible promoter. In a preferred embodiment of the invention the ipt gene is placed under the control of a glucocorticoid inducible promoter within a plasmid. In an alternate preferred embodiment the CKI1 gene or one of the genes of the knotted family is placed under the control of a glucocorticoid inducible promoter within a plasmid. The dexamethasone inducible system consists of a hybrid transcription factor that mediates transcription from the glucocorticoid receptor in the presence of DEX. This system allows tightly regulated ipt expression in transgenic plants. Plant cells are transformed with this plasmid and the cells are grown on MS medium without plant hormones but in the presence or absence of dexamethasone, a synthetic glucocorticoid analog. Under inductive conditions, cells transformed with the ipt gene will have elevated cytokinin levels and will regenerate shoots from plant calli or explants. Since the cells are grown in the absence of plant hormones, shoots will develop only in cells that are transformed and overproduce cytokinins in the presence of dexamethasone. Nontransformed cells will not produce shoots and cells grown in the absence of dexamethasone will not produce shoots. Overexpression of the ipt gene can thus serve as an antibiotic-free marker system that specifically selects for transformed cells. This system could also serve as a second marker to introduce additional genes into plants that are already resistant to antibiotics. Teratoma shoots should appear in 2–3 weeks on transformed cells grown in the presence of dexamethasone. These shoots can be excised and placed on MS medium containing indole acetic acid but without dexamethasone. Under this condition, the ipt, CKI1 or knotted gene should no longer be activated and after the cytokinin level has decreased to the normal level the transgenic plants should appear normal and fertile and be able to set seeds.

It must be noted that although some plants behave as described above (the only shoots produced are those from transformed plants), some plants may grow shoots in hormone free medium even if they are not transformed. A variety of techniques may be used with such plants to yield successful results of selecting transformed plants. One such method is that although shoots may be produced by non-transformed plants, such shoots look normal (wild-type) whereas transformed plants have the shooty phenotype. Therefore one can use the phenotype to distinguish transformed shoots from nontransformed shoots. An alternative method is to add a hormone such as an auxin to the growth medium to suppress shoot formation from nontransformed explants. This will decrease the background noise level of nontransformed shoots appearing. The amount of auxin to be added can be determined by a titration, i.e., using different concentrations of auxin, to determine the level which suppresses growth of shoots in nontransformed explants but allows shoot growth in transformed explants.

Figure 8:
FIG. 8 shows dexamethasone-dependent regeneration of tobacco and lettuce shoots. Leaf discs from tobacco (upper row) and lettuce (lower row) were transformed with the transformation cassette shown in FIG. 12. The plant materials were then grown for 40 days under inductive (10 μM DEX) or non-inductive (0 μM DEX) conditions.
Figures 10A, 10B, 10C, 10D:
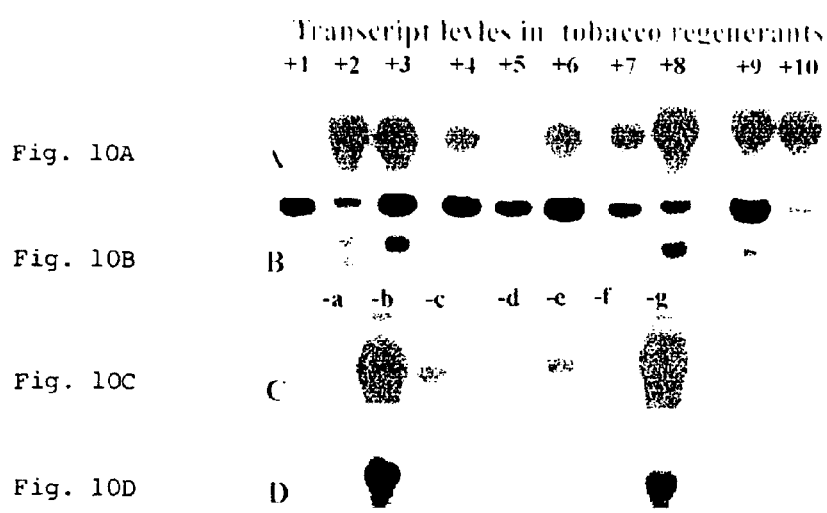
FIGS. 10A–D show Northern analysis of ipt and luc transcripts from tobacco. The level of ipt and luc transcripts from 30 day-old regenerants that had (+1 to +10) or did not have (−a to −g) detectable luciferase activity are shown. The regenerants were grown in the presence of 10 µM dexamethasone.
Figures 11A, 11B, 11C:
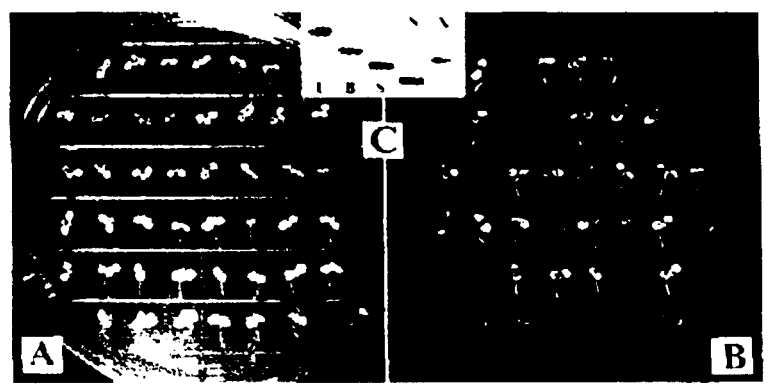
FIGS. 11A–C show segregation and Southern analysis of the luc gene in transgenic tobacco seedlings. Luciferase activity was measured in 44 randomly selected seedlings. Thirty-three of the seedlings displayed luciferase activity and eleven of the seedlings did not display luciferase activity (compare FIGS. 11A and 11B), demonstrating 3:1 segregation of the dominant luc gene. Southern blot analysis of DNA from the seedlings is shown in FIG. 11C. Single bands were detected with uncut DNA (U) and after DNA was digested with BamHI (B), SacI (S), NcoI (N), and XbaI (X) and hybridized with radioactively labeled fragments of the luc gene.

In one embodiment of the invention a transformation cassette (FIG. 12) containing the ipt gene under the control of the GVG glucocorticoid inducible system (Aoyama and Chua, 1997) acting as an antibiotic-free marker was used for the co-transformation of two other constitutively expressed genes (hygromycin phosphotransferase (hpt) and firefly luciferase (luc)). When induced with DEX, isopentenyl transferase was expressed from the ipt gene, leading to elevated cytokinin levels. Under inductive conditions for ipt expression, the elevated cytokinin levels led to efficient regeneration of transgenic shoots from tobacco or lettuce explants (FIG. 8). Determination of the ipt transcript levels in the regenerants revealed that regeneration was tightly coupled to ipt expression (FIGS. 10A–D). Even under non-inductive conditions where only a few shoots were regenerated from the explants, at least 50% of the regenerants contained the transgene. Southern and segregation analyses of transgenic shoots and plants revealed that the majority of regenerants contained only a single copy of the ipt gene (FIGS. 11A–C). Time course experiments demonstrated that regeneration was rapid and the specificity of the process was maintained over a time period of at least 20 days. The effects of the cytokinins were thus local and the hormones did not diffuse and trigger the regeneration of untransformed cells. This finding is in good agreement with the observation that even high exogenously applied concentrations of cytokinin cause more or less local reactions. The efficiency of the co-transformation of the hpt and luc genes was determined by measuring Luc activity (FIGS. 9A–F) and analyzing regenerants for hygromycin resistance. Northern analysis was also performed to determine hpt and luc transcript levels (FIGS. 10A–D). In about 80% of the shoots the luc and hpt genes were successfully co-transformed with the ipt inducible system. After the regenerants were transferred to non-inductive conditions the morphology of the tobacco and lettuce plants was completely normal. More than 40% of the tobacco regenerants developed strong root systems within 20 days and could easily be transferred to soil. The resulting plants showed no morphological or developmental abnormalities and the transgenes were transmitted to the progeny. These results demonstrate the advantages that inducible ipt expression has over constitutive expression of ipt.

In another embodiment of the invention, antibiotic or herbicide resistance genes are placed under the control of a glucocorticoid receptor inducible promoter. The promoter can be induced to allow for the expression of the antibiotic or herbicide resistance genes in order to select for transformed plant cells. Once transformed plant cells have been selected, the expression of the antibiotic and herbicide resistance genes can be repressed. This system is more environmentally sound than a system in which the transformed plants constitutively express active antibiotic or herbicide resistance genes.

The chemically inducible system can be used more generally and of course is not limited to being used to induce the ipt, CKI1 or knotted gene or other selectable marker. It can be used to chemically induce any gene of interest. It can be used to induce a screenable marker, such as luciferase or other desired screenable marker.

The development of the system which is used took place as a series of steps to test the individual aspects of the final construct. These steps are set out in the following Examples. A brief introduction explaining the progression of the experiments is first set forth here. The GVG system was first used to show that a construct could be made which would include a gene inducible by DEX or a glucocorticoid analog. The plasmid pMON721 was used for this purpose with luc being placed under the control of UAS. This was used to make transgenic tobacco plants which were selected on kanamycin medium. These experiments showed that such a system would work (Aoyama and Chua, 1997). Next, with the desire to avoid antibiotic resistance as a marker, new constructs were designed to use the ipt gene as a marker. Constructs were made with pTA7001 or pTA7002 vectors with multicloning sites downstream of the 6×UAS. These constructs included the GVG chimeric transcription system under a 35S promoter and also included a hygromycin-resistance gene regulated by the NOS promoter. The ipt gene was placed downstream of 6×UAS. Use of this construct demonstrated that the "shooty" phenotype resulting from ipt overexpression could be used as a marker. Different constructs were then made to extend the results to plants other than tobacco. The PTA7002/ipt construct was modified so that the 35S promoter, which is used to express the GVG coding sequence, was replaced with a synthetic promoter called G10-90 which acts as a stronger promoter than the 35S promoter. This consists of 4 copies of a G box fused to the -90 35S promoter. Furthermore, an additional gene, 35S-luc was added. This construct was used in both tobacco and lettuce plants. Selected shoots were then tested for luciferase expression and hygromycin resistance. The results indicate that a very high percentage of the shooty regenerants showed both luciferase expression and hygromycin resistance. This proves that use of the GVG system and the ipt gene allows one to use the shooty phenotype as a marker in different plants.

The present invention is described by reference to the following Examples, which are offered by way of illustration and are not intended to limit the invention in any manner. Standard techniques well known in the art or the techniques specifically described below were utilized.

EXAMPLE 1

DNA Constructs

A) Construct pTA7002

Plasmid pTA7002 is similar to pBI101 (Clontech) except that the sequence between the right border and the left border is replaced by three transcription units. The insert between the right and left borders of pTA7002 is illustrated in FIG. 1 and comprises a plasmid which includes the following elements: a 35S promoter, a GAL4 DNA binding domain, a VP16 transactivating domain, glucocorticoid receptor regulatory domains and a pea ribulose bisphosphate carboxylase small subunit rbcS-E9 poly(A) addition sequence all as part of a first transcription unit (35S-GVG-E9); a nopaline synthase (NOS) promoter, hygromycin phosphotransferase coding sequence, and the NOS terminator as part of a second transcription unit (NOS-HPT-NOS); and 6 tandem copies of a GAL4 upstream activating sequence (UAS) placed upstream of a minimal 35S promoter (−46 to +8) including the TATA region as part of a third transcription unit (6×UAS-(−46/35S)-3A). This third transcription unit also includes restriction sites (XhoI and SpeI) for insertion of any desired coding sequence and the pea ribulose bisphosphate carboxylase small subunit rbcS-3A (Fluhr et al., 1986). A coding region which is inserted in the XhoI-SpeI site should contain both the initiation and termination codons.

In more detail, the 35S-GVG-E9 transcription unit includes bases −343 to +9 of the CaMV 35S promoter (Odell et al., 1985). The GAL4 DNA binding domain comprises amino acids 1–74 (Laughon and Gesteland, 1984). The VP16 acidic domain comprises amino acids 413–490 (Dalrymple et al., 1985). The GR receptor domain comprises amino acids 519–795 (Miesfeld et al., 1986). The 3' end of this transcription unit is the poly(A) addition sequence of the pea ribulose bisphosphate carboxylase small subunit rbcS-E9 (Coruzzi et al., 1984). The 35S promoter which drives the GVG gene can be changed to a promoter fragment of choice using the Sse83871 and PmeI restriction enzyme sites. By doing so, a promoter can be inserted which can induce the inserted gene in a specific tissue or during a specific period depending on the characteristics of the promoter.

B) pTA7001

This plasmid is identical with pTA7002 except for the orientation of the fragment containing 6×GAL4 UAS-TATA-cloning sites-3A terminator. Therefore it also contains both the cis- and trans-elements in the T-DNA region of the plasmid. The trans-element is the GVG region consisting of the GAL4 DNA binding domain, the VP16 transactivating domain, and the GR receptor domain driven by the 35S promoter. The cis-element consists of 6×GAL4 UAS and the TATA region of the 35S promoter. Again, this plasmid is based upon pBI101(Clontech) with the region between RB and LB having been replaced. In pTA7001 this region has become:

1–39: pTiPOST37 from pBI101 (RB=1–25)
47–858: 35S promoter from pBI221 (TATA=813–816)
867–1097: GAL4 (aa 1–77)
1117–1340: VP16(aa 413–490)
1347–2180: rat GR (aa 519–795)
2207–2764: pea rbcs-E9 terminator
2780–3112: NOS promoter from pBI101
3120–4145: hygromycin phosphotransferase
4147–4399: NOS terminator from pBI101
4893–4423: pea rbcs-3A terminator
4941–4894: cloning sites XhoI, SpeI
4995–4942: 35S promoter TATA region (TATA= 4980–4977)
5197–4996: 6×GAL4 UAS
5198–5357: M13 mmp19 EcoRI-HaeII fragment from pBI101
5358–5862: pTiPOST37 from pBI101 (LB=5838–5862).

C) pTA7002/ipt

This plasmid was prepared by inserting a restriction fragment (XhoI, SpeI) containing the isopentenyltransferase (ipt) gene of the pTiT37 plasmid (Goldberg et al., 1984) downstream of the 6×UAS promoter in the pTA7002 plasmid.

D) pMON721/Luc

Figure 2:
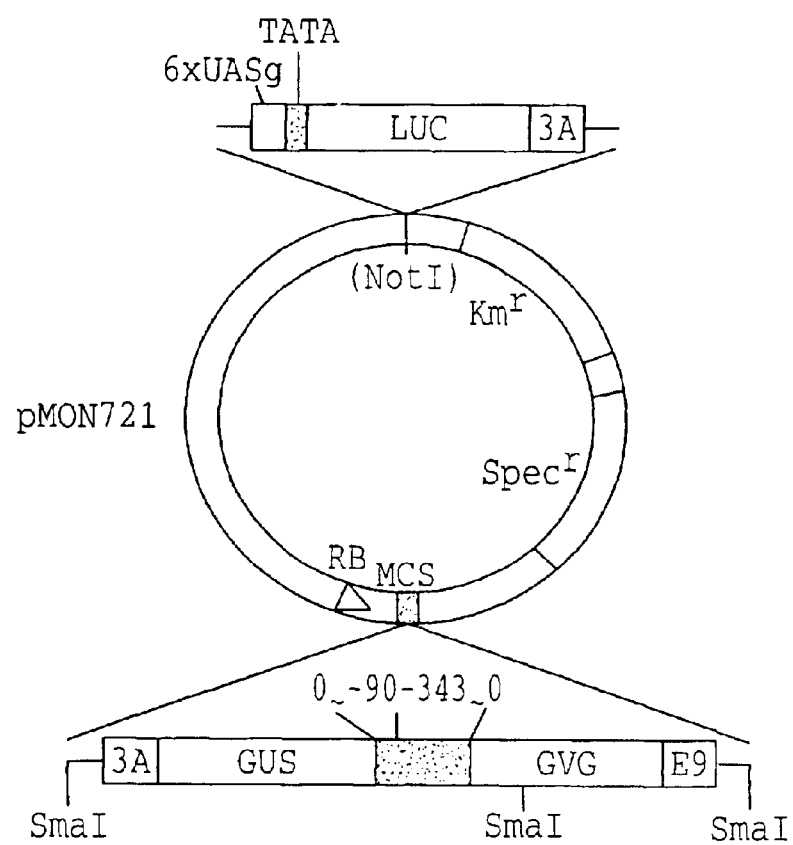
FIG. 2 illustrates the insertion points into pMON721 of the luciferase and the GVG constructs. The luciferase is inserted into the Not I restriction site. The GVG is inserted into the multicloning site of the vector.

This plasmid is similar in design to the pTA7002 plasmid in that it incorporates the same GVG system. However, this is based upon the pMON721 vector (Monsanto Corp., St. Louis, Mo.) rather than the pTA7002 plasmid. The GVG gene, which is transcribed from the −343 to +1 region of the CaMV 35S promoter (Odell et al., 1985), was flanked at the 3' end by the poly(A) addition sequence of the pea ribulose bisphosphate carboxylase small subunit rbcS-E9 (Coruzzi et al., 1984). The DNA fragments encoding specific domains were produced by the polymerase chain reaction (PCR) using primers of appropriate sequences for in-frame cloning. The GAL4 DNA binding domain comprises amino acids 1–74 (Laughon and Gesteland, 1984), the VP16 acidic domain comprises amino acids 413–490 (Dalrymple et al., 1985), and the GR receptor domain comprises amino acids 519–795 (Miesfeld et al., 1986). The GAL4 UAS DNA (5'-CGGGTGACAGCCCTCCG-3' SEQ ID NO:1) was synthesized chemically and the coding sequence for the luc gene (de Wet et al., 1987) was excised from pGEM-luc (Promega Co.). The Luc coding sequence was transcribed from six copies of GAL4 UAS placed 5' to the −46 to +1 region of the 35S promoter and flanked at the 3' end by the poly(A) addition sequence of the pea rbcS-3A (Fluhr et al., 1986). FIG. 2 illustrates the points of insertion into pMON721 of the GVG and luc nucleic acid constructs.

E) pTA7002G/ipt/luc (pYS4)

This plasmid is similar to pTA7002ipt but with two differences. The 35S promoter of the pTA7002/ipt vector was replaced with a synthetic promoter called G10–90. This latter promoter consists of 4 copies of a G box (GCCACGTGCC SEQ ID NO:2) fused to the −90 35S promoter. Also, a 35S-luc gene was included to facilitate visual recognition of transformants using a sensitive imaging system. This vector is shown in FIG. 12. See, Kunkel et al., 1999.

F) XVE Vectors

The backbone of the XVE vectors pER8 and pER10 (see FIG. 13) are pTA211 and pTA221 (Kost et al., 1998), respectively. XVE: a chimeric transcription factor containing the DNA-binding domain of LexA (residues 1–87), transactivating domain of VP16 (413–490) and the regulatory region of the human estrogen receptor (272–595). The second expression cassette, which controls the gene of interest, was made by fusing 8 copies of LexA binding sites to −46 of the 35S minimal promoter.

pER8-CKI1 (XVE-CKI1): an XhoI/SpeI DNA fragment containing the coding as well as part of the 5'- and 3'-untranslated region of the CKI1 cDNA was inserted into the same sites of pER8 vector downstream from the 8XLexA−46 promoter. In this construct, the CKI1 gene was thus placed under the control of the XVE inducible system, and its transcription can only be activated by 17-β-estradiol or 4-hydroxyl tamoxifen.

pER8-Lex1(XVE–Lec1): an XhoI/SpeI DNA fragment containing the coding as well as part of the 5'- and 3'-untranslated region of the Lec1 cDNA was inserted into the same sites of pER8 vector downstream from the 8XLexA-46 promoter. In this construct the Lec1 gene was thus placed under the control of the XVE inducible system, and its transcription can only be activated by 17-β-estradiol or 4-hydroxyl tamoxifen.

pER8-SERK (XVE-SERK): a genomic DNA fragment containing the Arabidopsis SERK gene (without the SERK promoter and the transcription termination sequences) was inserted into the same sites of pER8 vector downstream from the 8XLexA−46 promoter. In this construct, the SERK gene ws thus placed under the control of the XVE inducible system, and its transcription can only be activated by 17-β-estradiol or 4-hydroxyl tamoxifen.

EXAMPLE 2

Plants Transformed with pMON721 Based Vectors

The vector pMON721 can be used in combination with *A. tumefaciens* strain ABI but is not used with *A. tumefaciens* strain LB4404. Strain ABI alone can induce shoots on tobacco leaf discs cultivated on MS medium without hormone and is therefore unusable for experiments in which the marker is the growth of shoots. The pMON721-*A. tumefaciens* strain ABI combination is useful for those experiments in which other markers are being screened, e.g., when one is selecting for antibiotic resistance. In these experiments the cells are grown in medium with hormones and selection is by kanamycin resistance, and they are grown both in the presence and in the absence of the inducer, e.g., dexamethasone.

A) Transformation of Plasmid into Bacteria

Plasmids were introduced into *Agrobacterium tumefaciens*. Plasmids derived from pMON721 were placed into strain ABI (Monsanto Corp., St. Louis, Mo.) by methods well known by those of skill in the art. For example, for pMON721/Luc, a single colony of *Agrobacterium tumefaciens* strain ABI (Monsanto Corp., St. Louis, Mo.) containing pMON721/Luc was selected from YEB plates containing 50 mg/L kanamycin, 25 mg/L chloramphenicol, 100 mg/L spectinomycin and 100 mg/L streptomycin. The Agrobacterium cells were transferred to a 50-mL sterile screw cap tube containing 10 mL YEB liquid medium with 50 mg/L kanamycin, 25 mg/L chloramphenicol, 100 mg/L spectinomycin and 100 mg/L streptomycin. The culture was grown at 28° C. for 24 hours. Agrobacterium cells in culture were collected by centrifugation at 3,000 rpm at 4° C. for 10 minutes. The cell pellet was washed once in 10 mL of YEB medium with antibiotics and then resuspended in 30 mL of B5 medium, which was used for inoculation of explants. YEB medium is prepared by bringing to 1.0 liter the following: 5.0 grams sucrose, 5.0 grams peptone, 5.0 grams beef extract, 1.0 gram yeast extract and 0.04 gram $MgSO_4 7H_2O$.

B) Co-cultivation with Agrobacteria

Leaf discs of *Nicotiana tabacum* cv SR1 were transformed and regenerated as described by Horsch et al. (1988) and transformation of Arabidopsis was performed according to the method of Valvekens et al. (1988).

C) Luciferase Containing Transgenic Plants

Primary transgenic plants were allowed to self-fertilize and seeds were collected. The transgenic progeny were germinated on MS medium (Murashige and Skoog, 1962) supplemented with 3% sucrose, 0.8% agar and 100 µg/mL kanamycin for selection. $T_3$ homozygous plants grown on the same agar medium for 14 days after germination were used in induction experiments. In some experiments, plants were transferred to a hydroponic growth medium containing 1/100 concentration of MS salts and adapted to the growth conditions for 3 days before use. In all cases, plants were exposed to continuous light and a temperature of 27° C. (tobacco) or 22° C. (Arabidopsis).

EXAMPLE 3

Plants Transformed with PTA7002 or PTA7001 Based Vectors

The vectors pTA7002 and pTA7001 may be used with *A. tumefaciens* strain LB4404. Unlike *A. tumefaciens* strain ABI, the LB4404 strain does not induce shoots and this combination of vector and bacterial strain may be used in those experiments in which the growth of shoots is the marker. The experiments described here used pTA7002/ipt. However, the vector used may include other genes of interest which are not under the control of the GVG system, which other genes it is desired to transform into plants. In these experiments, plants are selected on medium without hormones and without antibiotics, but in the presence and in the absence of inducer (e.g., dexamethasone). Only those cells grown in the presence of the inducer should generate shoots. These shoots are cut, placed in medium with auxins but without the inducer. The absence of the inducer stops the transcription of the ipt gene and auxin in the medium promotes root regeneration. These can then be tested by Northern blot analysis or for resistance to hygromycin to determine which regenerated plants in fact are transformed.

A) Transformation of Plasmid into Bacteria

Plasmids were introduced into *Agrobacterium tumefaciens*. Plasmids derived from pTA7002 or pTA7001 were placed into strain LB4404 (Clontech Laboratories, Inc.) by methods well known by those of skill in the art. For example, for pTA7002/ipt, a single colony of LB4404 containing pTA7002/ipt was selected from YEB plates containing 50 mg/L kanamycin and 100 mg/L streptomycin. The Agrobacterium cells were transferred to a 50-mL sterile screw cap tube containing 10 mL YEB liquid medium with 50 mg/L kanamycin and 100 mg/L streptomycin. The culture was grown at 28° C. for 24 hours. Agrobacterium cells in culture were collected by centrifugation at 3,000 rpm at 4° C. for 10 minutes. The cell pellet was washed once in 10 mL of YEB medium with antibiotics and then resuspended in 30 mL of B5 medium, which was used for inoculation of explants.

B) Co-cultivation with Agrobacteria

Tobacco leaves were cut into sections of 4 mm×4 mm on a wet sterile filter paper and then transferred to sterile, deionized water. The leaf sections were immersed for several minutes in the Agrobacteria solution (in B5 medium) in a petri dish. The sections were blotted dry on a piece of sterile filter paper and then placed on MBDK plates. MBDK media composition is: MS salts–4.3 g/L; B5 vitamins–112 mg/L; 2–4-D–0.5 mg/L; kinetin–0.1 mg/L; sucrose–20 g/L; phytagel–2 g/L; pH 5.7.

C) Shoot Regeneration

After 3 days of co-cultivation of tobacco leaves with Agrobacteria, the explants were washed 3 times by immersions in 30 mL sterile water containing 200 mg/L carbenicillin in a petri dish. After having blotted dry on sterile paper toweling, the explants were placed on MBC medium with or without dexamethasone (DEX, 30 µM). MBC media composition is: MS salts–4.3 g/L; B5 vitamins–112 mg/L; sucrose–20.0 g/L; carbenicillin–200 mg/L; phytagel–2.0 g/L; pH 5.7. The plates were incubated in a tissue culture room at 25° C. and 16 hour light/8 hour dark. After two weeks, green shoot buds appeared at wound sites of the explants only on medium containing DEX (30 µM). The shoots were excised and transferred to MBCI plates. MBCI medium is: MS salts–4.3 g/L, B5 vitamins–112 mg/L, sucrose–20.0 g/L, carbenicillin–200 mg/L, phytagel–2.0 g/L, pH 5.7, indole acetic acid (IAA)–0.15 mg/L.

D) Selection of Transgenic Plants

After 10 days of culture on MBCI plates, many adventitious shoots appear. These are cut and transferred to new MBCI plates. These shoots become normal looking after 10 days of culture. They regenerate roots and grow to plantlets of 4–6 leaves after 2–3 weeks. At this stage, they are ready to be tested to verify whether they are indeed transformed. Since the pTA7001 or pTA7002 plasmid contains a NOS-Hpt gene, transformed shoots should be resistant to hygromycin. Therefore, leaf samples containing petioles are excised and transferred to MBCI medium with 40 mg/L hygromycin for root induction. Only ~10% of the shoots collected are actually transformed. Nontransgenic cells may form shoots as a result of absorbing cytokinins produced from neighboring cells which are transformed and are producing cytokinins. Growth of the selected shoots in the presence of hygromycin can be used to select for transformed shoots. Northern or Southern blot analysis is another means of testing for transformation. These latter methods are useful in experiments in which the NOS-hpt gene has been deleted from the pTA7001 or pTA7002 plasmid and a gene of interest has been inserted in its place. Rooted shoots are transferred to pots and grown to maturity in a greenhouse. The transgenic plants appear normal and are fertile and set seeds.

EXAMPLE 4

Induction with Glucocorticoid

All glucocorticoid derivatives, dexamethasone (DEX), triamcinolone acetonide, betamethasone and hydrocortisone were purchased from Wako Pure Chemical Industries. The chemicals were dissolved in ethanol at 30 mM before use and diluted in either the growth medium or the spraying solution. The same volume of ethanol was added to negative control medium or solution. In the case of tissue culture experiments (as in Example 3) DEX is included in the tissue culture medium with phytagel. In the case of whole-plant treatment, plants were grown on an agar medium containing glucocorticoid or their roots were submerged in a hydroponic growth medium containing glucocorticoid at 0.01 mM. For the spraying method, the solution contained 30 $\mu$M DEX and 0.01% (w/v) Tween-20; the latter was added as a wetting agent. In experiments involving spraying of one half of a leaf, the other half and other parts of the plant were covered with a plastic film. It should be noted that although DEX is not an especially toxic chemical, it could have some physiological effect on a human and one should take precautions, especially the use of eye protection when one is spraying the compound.

EXAMPLE 5

Luciferase Assays

Extraction of luciferase and assays for relative luciferase activities were carried out as described by Millar et al. (1992). To image the luciferase luminescence, roots of plants treated with DEX were submerged in a solution containing 0.5 mM potassium luciferin (Sigma) for 1 hour or the petiole of a sprayed leaf was submerged in a solution of 0.5 mM potassium luciferin for 30 minutes. Potted plants were sprayed with a solution containing 0.5 mM potassium luciferin and 0.01% (w/v) Tween-20 and left for 30 minutes. The luciferase luminescence from plants was visualized using an image-intensifying camera (VIM) and photon-counting image processors (ARGUS-50) purchased from Hamamatsu Photonic Systems. The exposure time was 10 minutes. To take a picture of the luciferase luminescence from the sprayed leaf, the leaf and an instant color film (LP100, Fuji Photo films co.) were placed in contact with one another, with a thin plastic film between them, for 5 hours.

EXAMPLE 6

RNA Analysis

Total RNA isolation and Northern blot hybridization were performed as described by Nagy et al. (1988). After hybridization, signals were imaged with the BAS-2000 system (Fuji Photo Films Co.).

EXAMPLE 7

Selection of the Best Transgenic Lines

Several independent transgenic lines should be obtained and tested. One should select the best line as that which has a low basal level and a high induction level. Multicopies of DNA fragment are often inserted into one locus. In such a case, the 35S-promoter near the RB might happen to neighbor the inducible promoter and change the inducible promoter to a constitutively active promoter. Other than such a case, a chromosomal sequence neighboring the inducible promoter might also affect the activity. Therefore it is best to test the obtained transgenic lines to find one which has low basal activity and a high induction level.

EXAMPLE 8

Induction of Luciferase Activity in Transgenic Plants

Figure 3A:
FIG. 3A is a scale showing the luminescence intensity from dark gray (lowest) to white (highest). Although shown as a scale of dark gray to white, in fact the luminescence is a blue color. This scale is used for interpreting the results of FIG. 3B.
Figure 3B:
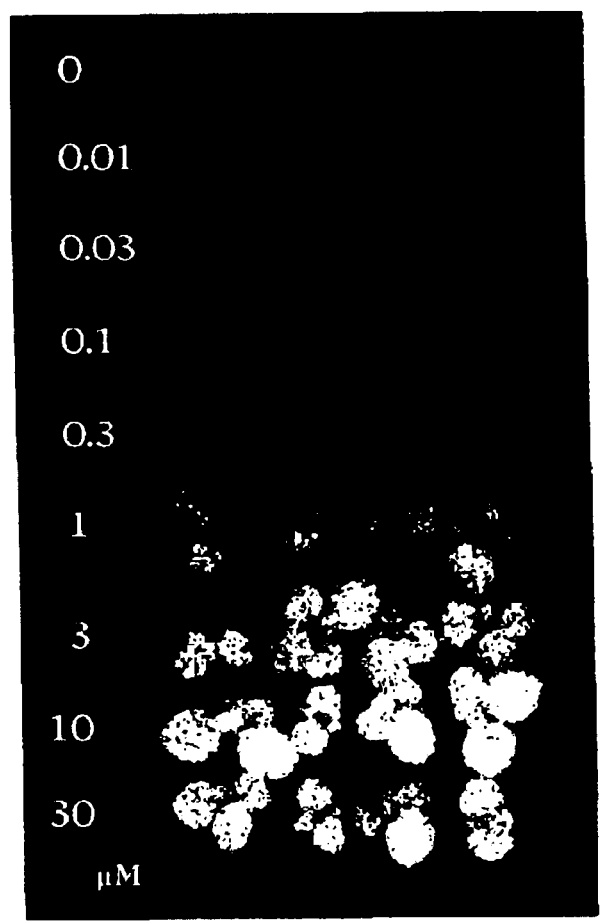
FIG. 3B shows the stationary expression levels of the luciferase activity induced by different concentrations of DEX.
Figure 3C:
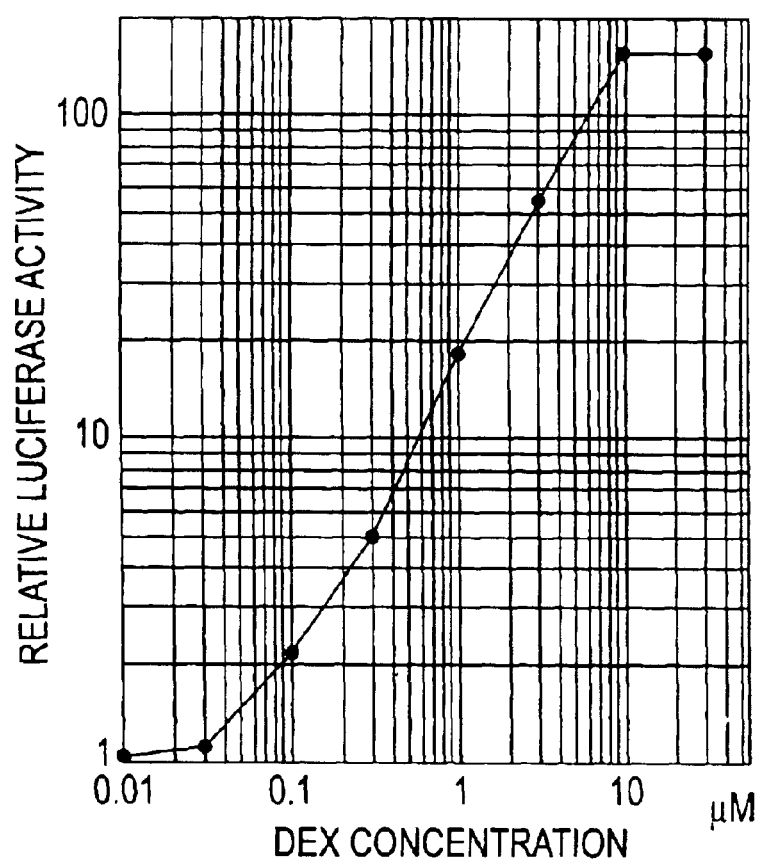
FIG. 3C shows the results of FIG. 3B plotted against DEX concentrations. The value obtained at 0 μM DEX (the basal, non-induction level) was arbitrarily set as 1.

Stationary induction levels of the luciferase activity were measured in response to different concentrations of a glucocorticoid. Young transgenic plants (prepared using the pMON721/luc vector) grown on an agar medium were transferred to a fresh agar medium containing different concentrations of DEX. After 2 days on the induction medium, whole cell lysate was prepared from 10 plants and assayed for luciferase activity. FIG. 3B shows an image of luciferase luminescence from plants using a high-sensitivity camera system. The color scale for FIG. 3B is shown in FIG. 3A. FIG. 3C shows the relative luciferase activity induced by different concentrations of DEX. The luciferase activity detected in the absence of DEX was very low and comparable to that obtained from transgenic plants carrying a luciferase gene preceded by the TATA region only (data not shown). This result indicates that the GAL4 UAS was quiescent in plants and not recognized by any endogenous plant transcription factor. Induction was detectable at a concentration of 0.1 $\mu$M DEX or higher, and a good correlation between DEX concentrations and induction levels was obtained in the concentration range from 0.1 to 10 $\mu$M. The maximum induction level was 100 times the basal level.

In this experiment, plants were treated with DEX for a sufficiently long period to ensure that the luciferase activity had reached a plateau for each DEX concentration. Induction was very slow in plastic wares, as observed in this experiment, probably because, under the enclosed conditions, transpirational water flow in plants and hence the uptake of glucocorticoid through the roots was slow compared with that under non-enclosed, open-air conditions. On the other hand, under the latter conditions, it is very difficult to precisely control the glucocorticoid concentration in plants because the hormone rapidly accumulates in leaves, as a result of transpiration.

Various plant species have been employed for studies on basic and applied aspects of plant sciences, and among them, Arabidopsis has emerged as a model plant for basic explorations of plant biology. So far, however, good induction systems have not yet been developed for this model plant.

Figure 4A:
FIGS. 4A–C represent the induction of luciferase activity in Arabidopsis.
Figure 4B:
Figure 4C:
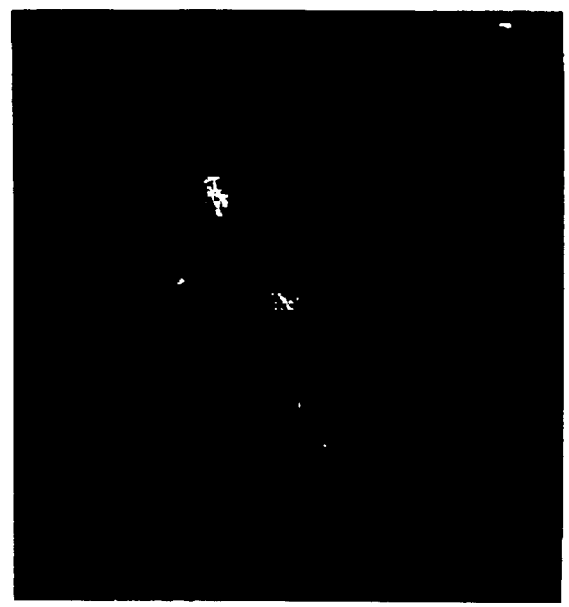

Induction systems using plant promoters, e.g., heat-shock promoters, are not suitable because they elicit pleiotropic effects. Although the tetracycline-dependent expression system has been successfully used in tobacco, it does not appear to function in Arabidopsis (Gatz, 1996). On the other hand, it is seen here that the GVG system can also function in Arabidopsis. FIGS. 4A–C show that the luciferase activity in transgenic Arabidopsis was induced effectively by DEX. The GVG system should be widely applicable to many genes and in different species of transgenic plants.

EXAMPLE 9

Kinetics of the Transcriptional Induction by DEX

Figure 5A:
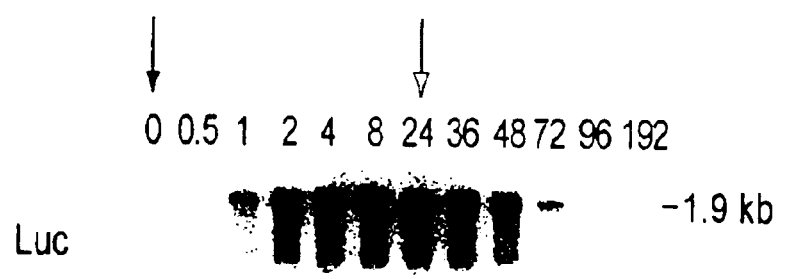
FIGS. 5A–B represent the kinetics of the luc mRNA level induced by DEX. Transgenic tobacco plants carrying the GVG gene and the luc reporter gene were first grown on agar medium for 14 days and then adapted to growth in a hydroponic medium for 3 days. DEX treatment was started by adding DEX to the medium at a final concentration of 10 μM (time indicated as 0). After 24 hours of treatment, DEX was then removed from the medium. Total RNA was prepared from 20 plants at each time indicated and subjected to Northern blot analysis. cDNA fragments of the firefly luciferase (FIG. 5A) and the GVG gene (FIG. 5B) were used as probes. Signals were imaged by the BAS-2000 system (Fuji Photo Films co.). Closed and open arrows indicate the time points of adding and removing DEX, respectively.
Figure 5B:

Although the luciferase activity is easy to measure, it is not suitable for kinetic study within a short time scale because the half-life of luciferase activity is estimated to be approximately 3 hours (Thompson et al., 1991). To obtain more direct information on the kinetics of induction, total RNA was prepared and subjected to Northern blot analysis. In these experiments, plants were placed in the open air to ensure rapid DEX uptake. Transgenic plants were adapted to hydroponic growth conditions in the open air and DEX was added to the liquid growth medium at a final concentration of 10 $\mu$M. Total RNA was prepared from 20 plants at each time point and subjected to Northern blot analysis. Results for plants transfected with pMON721/luc are shown in FIGS. 4A and 5A. FIG. 4A shows that the luc mRNA was first detected 1 hour after the addition of DEX and the amount increased to a stationary level within the next 3 hours. To examine the sustainability of the induction, DEX was removed from the medium and total RNA prepared from the plants was analyzed. FIG. 5A shows that luc mRNA could be detected even 4 days after removal of DEX.

A similar result was obtained by monitoring the luciferase activity. Due to the high sensitivity of detection, the induced luciferase activity could be measured 30 minutes after DEX addition and for 8 days after removal of the hormone (data not shown). From these results, it can be concluded that the transcriptional induction by DEX is rapid and can be maintained for a long period.

EXAMPLE 10

Responses to Various Glucocorticoids

Figure 6:
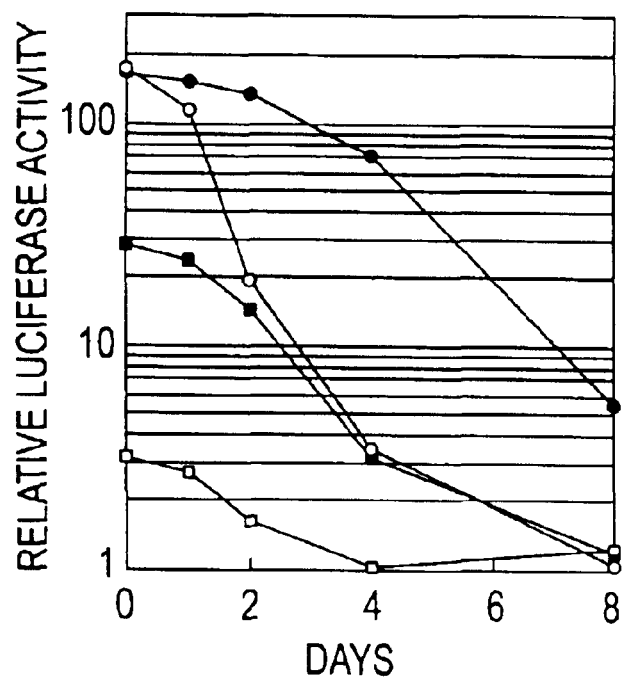
FIG. 6 shows the intensity and sustainability of induction by various glucocorticoids. Transgenic tobacco plants carrying the GVG gene and the luc reporter gene were first grown on agar medium for 14 days and then transferred to a fresh agar medium containing 30 μM of different glucocorticoids for an additional 2 days. After the induction, plants were transferred back to the agar medium without glucocorticoid (time indicated as 0). Relative luciferase activities induced by DEX (●) triamcinolone acetonide (○), betamethasone (■) and hydrocortisone (□) are plotted. The value obtained with no glucocorticoid (the non-induction level) was arbitrarily set as 1.

Different glucocorticoid derivatives were examined for the intensity and the duration of induction. Young transgenic plants (transfected with pMON721/luc) grown on an agar medium were transferred to a fresh agar medium containing 30 $\mu$M of different glucocorticoids and grown for an additional 2 days. After the induction, plants were returned to the agar medium without glucocorticoid. At each time point indicated in FIG. 6, 10 plants were harvested and their luciferase activities assayed. FIG. 6 shows that the induction levels and their durations were different with different glucocorticoid derivatives. The highest induction levels were obtained with either DEX or triamcinolone acetonide. In contrast, only low or moderate induction levels were detected with betamethasone or hydrocorticoid, respectively. In these experiments, it was assumed that the induction level obtained with each glucocorticoid had reached a steady-state level because longer induction periods did not significantly increase the luciferase activity (data not shown). The induction by DEX was maintained for a longer period compared with that by triamcinolone acetonide, whereas both glucocorticoids conferred about the same induction level at the beginning of the treatment. Although the stability of these glucocorticoids in plants is not known in these experiments, the induction characteristics of different glucocorticoids might be used to regulate the intensity and the duration of induction.

EXAMPLE 11

Local Induction of Luciferase Expression by Glucocorticoid Spraying

Figure 7:
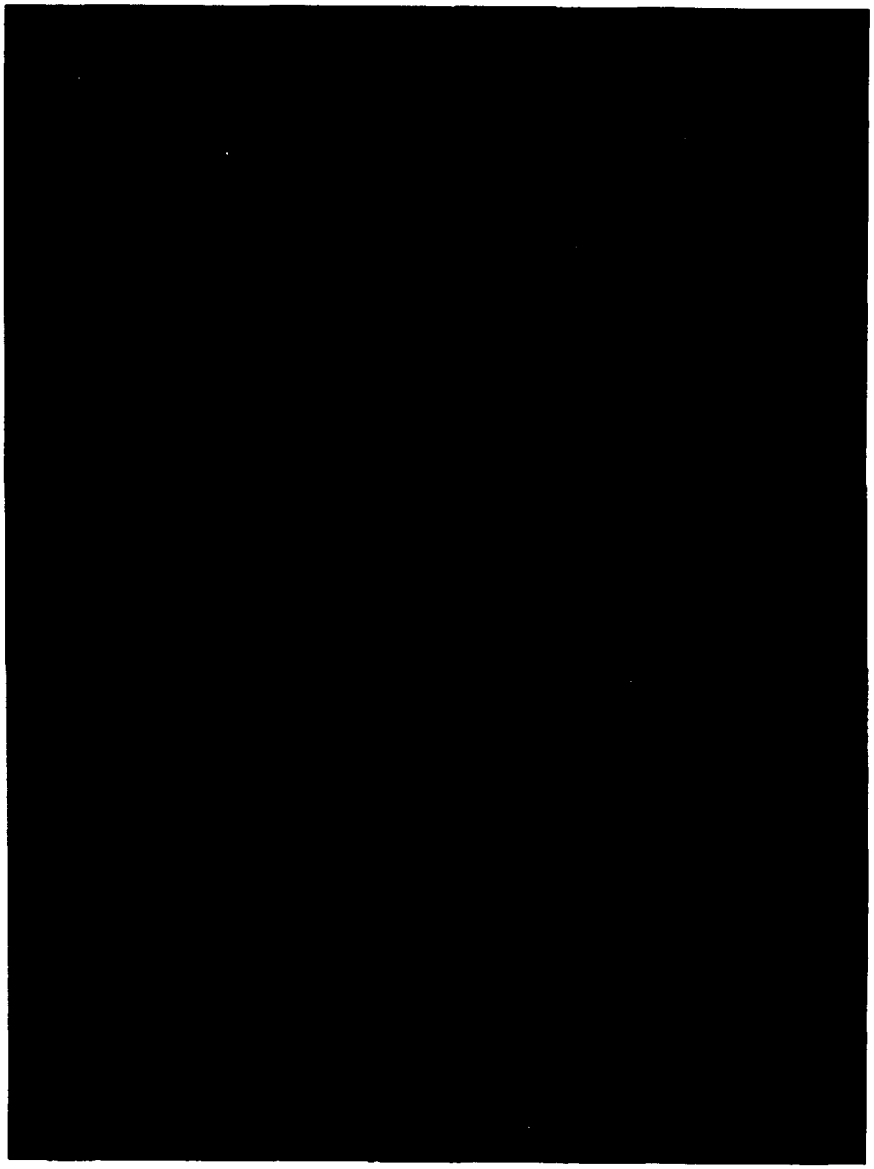
FIG. 7 shows the local induction of luciferase expression by glucocorticoid spraying.

The right and left halves of a leaf (about 10 cm in length) on a mature plant carrying the GVG and the Luc genes (the plant was transgenic for the pMON721/luc vector) were sprayed with a solution containing 30 $\mu$M DEX and 0.01% (w/v) Tween-20 and a control solution, respectively. Twenty-four hours after spraying, the leaf was excised and allowed to take up luciferin through the petiole. FIG. 7 shows fluorescence from the portion of the leaf which had been treated with DEX whereas no fluorescence is seen in the portion of the leaf treated with a control solution without DEX. FIG. 7 was taken by placing an instant color film (Fuji Photo Films Co. LP100) on to the leaf, with thin plastic film in between them, for 5 hours.

EXAMPLE 12

The XVE Inducible Expression System

It will be a great advantage in basic and applied sciences to independently and inducibly control the expression of multiple genes. As a first step toward this goal, we developed a new inducible expression system, designated XVE (see FIG. 13). Principally, the XVE system is similar to that of GVG, in which the regulatory region of a nuclear receptor confers the hormonal inducibility to the heterologous DBD fused to the former sequence. The XVE chimera contain the DBD of the bacterial repressor LexA (X) (Horii et al., 1981; Miki et al., 1981) and the regulatory region of human estrogen receptor (E) (Greene et al., 1986). These structural features allow XVE to have different DNA binding specificity and to be activated by different stimuli compared to GVG. Accordingly, eight copies of LexA binding sites were fused to the 35S minimal promoter at −46 to drive effector genes.

Figure 13:
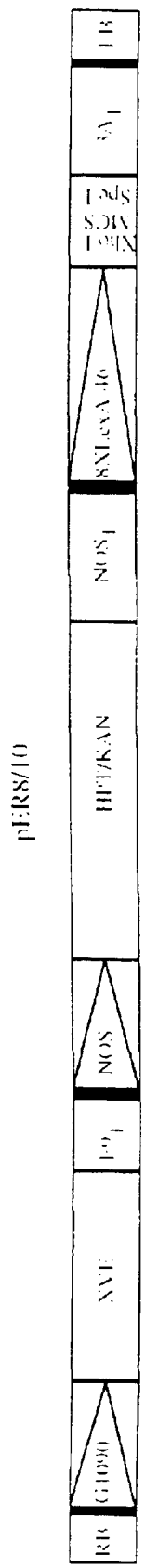
FIG. 13 is a schematic map of the XVE vectors. The backbone of these vectors are pTA211 and pTA221 (Kost et al., 1998), respectively. Only regions to be integrated into the plant genome (between the right border or RB and the left border or LB) are shown (not to scale). G1090: a synthetic promoter (Ishige et al., 1999) driving XVE; XVE: a chimeric transcription factor containing the DNA-binding domain (DBD) of LexA (residues 1–87), transcription activation domain of VP16 (413–490) and the regulatory region of the human estrogen receptor (272–595); $E9_T$: rbcs E9 polyA addition sequence; NOS: nopaline synthase promoter; HPT: hygromycin selection marker; KAN: kanamycin selection marker; $NOS_T$: nopaline synthase poly A addition sequence; 8XLexA: 8 copies of LexA repressor binding sites; −46: the 35S minimal promoter; $3A_T$: rbcs 3A polyA addition sequence; MCS: multicloning site.
Figure 14A:
FIGS. 14A–B show expression of the GFP gene controlled by the XVE inducible system.
Figure 14B:

To test the XVE system, we inserted a cDNA encoding the green fluorescence protein (GFP) into the effector cassette of an XVE vector (pER8; see FIG. 13 for details). The pER8-GFP vector was transformed into Arabidopsis and tobacco, and expression of the GFP gene was assessed. Similar results were obtained from both species. Here, we present data obtained from a detailed analysis of pER8-GFP Arabidopsis transgenic lines. We initially screened 22 independent transgenic lines by visual inspection of plants germinated in the absence (control) or presence (induced) of inducers (a mixture of 2 $\mu$M 17-β-estradiol and 1 $\mu$M 4-hydroxyl tamoxifen) under a conventional fluorescence microscope. The result of this screening is summarized in Table 1. High level induction was observed in more than half of the lines, and a representative example is given in FIG. 14. Among the remaining lines, the GFP gene either expressed at a lower level (23%) or, in a few cases, did not have detectable expression (9%). A small fraction of these lines expressed the GFP gene in a patchy pattern (14%). These data indicated that XVE is a highly efficient expression system. In all examined lines, no background expression (in the absence of inducers) was detected, suggesting that the system is tightly controlled.

TABLE 1

Summary of pER8-GFP Transgenic Arabidopsis Lines

| GFP Signal | # of Lines | % |
| --- | --- | --- |
| Strong | 12 | 54.5 |
| Weak | 5 | 22.7 |
| No Signal | 2 | 9.2 |
| Patchy | 3 | 13.6 |
| Total | 22 | 100 |

EXAMPLE 13

Characterization of the XVE Inducible Expression System

In the original screen, a mixture of 17-β-estradiol and 4-hydroxyl tamoxifen, two most commonly used inducers of estrogen receptors, were used. To distinguish which compound is the active form for the response, these two chemicals were separately tested for their inducibility. Whereas both chemicals were capable of inducing the expression of the reporter gene, 4-hydroxyl tamoxifen appeared to be slightly less active than 17-β-estradiol. The latter inducer was used in all subsequent experiments.

Figure 15:
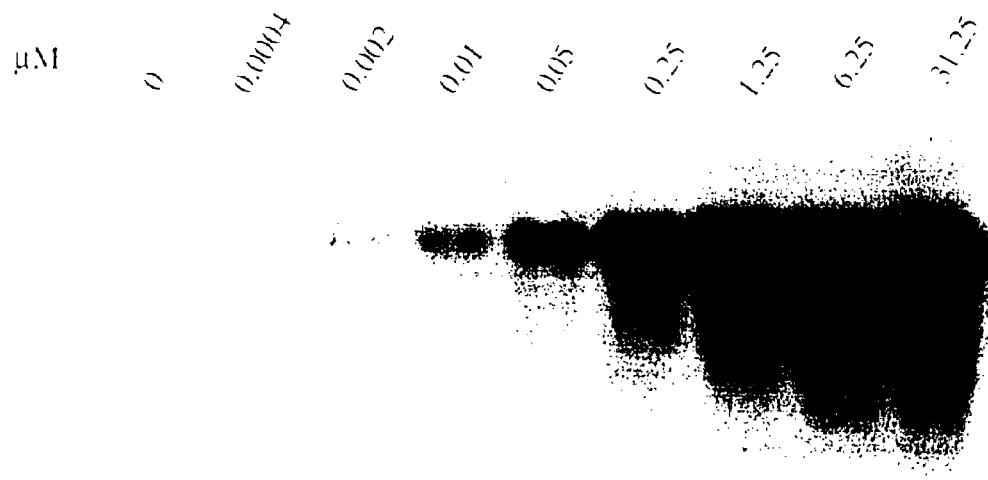
FIG. 15 shows the dose-dependence on 17-β-estradiol of the XVE inducible system. Three-week-old pER8-GFP transgenic plants cultured in the absence of the inducer were transferred onto medium containing various concentrations of 17-β-estradiol, and incubated for 16 hours. RNAs were prepared from not-treated (lane 0; control) or 17-β-estradiol-treated plants, and analyzed by Northern blotting using the GFP cDNA as a probe. Numbers above each lane indicate the concentrations (in micromolar) of the treatment.

To examine dose-dependence of the system, three-week-old seedlings germinated in the absence of the inducer were transferred to medium containing various concentrations of 17-β-estradiol, and incubated for 16 hours. RNAs were prepared from the not-treated (control) or treated seedlings, and analyzed by Northern blotting using the GFP cDNA as a probe. As shown in FIG. 15, the GFP transcript could be detected with treatment of 0.0004 $\mu$M (0.4 nM) 17-β-estradiol, and the induction was saturated at a concentration of approximately 1.25 $\mu$M.

Figure 16:
FIG. 16 shows the induction time-course of the XVE system. Three-week-old pER8-GFP transgenic plants cultured in the absence of the inducer were transferred onto medium containing 2 µM 17-β-estradiol, and incubated for various times (indicated in hours above each lane). Analysis of the GFP transcripts was carried out as described in FIG. 15.

In time course experiments, three-week-old seedlings were transferred to medium containing 2 $\mu$M of 17-β-estradiol, and incubated for various lengths of time. RNAs were prepared and analyzed as described before. The GFP transcript was detectable upon a 30-minute incubation, and the expression reached the maximum level after a 24-hour induction (FIG. 16). In separate experiments, the GFP fluorescence appeared unchanged upon five-week incubation on the induction medium, suggesting that the system remained constantly active.

Three independent transgenic lines were tested in experiments shown in FIGS. 15 and 16, and similar results were obtained. In both cases, a 100–200-fold induction of transcripts was routinely achieved. More importantly, no apparently toxic effects or physiological alterations were observed in all the tested lines. The above analyses indicate that XVE is an efficient and reliable inducible system.

EXAMPLE 14

Transfection of Tobacco Leaf Disks and Root Cells with XVE-CKI1

In addition to the GVG-ipt, pER8-CKI1 (XVE-CKI1) has been used to transfect tobacco leaf disks. Upon induction with 17-β-estradiol, shoots regenerated without using any externally applied plant hormones. Shoots initiated 25–35 days after induction. Addition of IAA (0.15 mg/L) did not increase efficiency, but rather had adverse effects on shoot formation. The regeneration efficiency was dose-dependent on 17-β-estradiol in the medium (tested at concentrations of 1, 5, 10, 20 and 30 $\mu$M with saturation occurring at 10 $\mu$M).

The XVE-CKI1 vector was also used to transform tobacco root cells. Using the root cells, shoots were regenerated after induction with 17-β-estradiol without using any externally applied plant hormones. 2,4-D (0.5 mg/L) arid kinetin (0.1 mg/L) were included when coculturing roots with Agrobacteria (2–3 days at 22° C.). Infected roots were placed on MBC medium with or without 17-β-estradiol (5 $\mu$M). The explants were transferred to fresh MBC medium (with or without the inducer) every two weeks. Explants grown in the absence of the inducer did produce white or dark-yellow calli after culturing for 20–30 days, but these would not form shoots. The explants grown in the presence of inducer formed green callus. Shoots initiated 40–50 days after induction. On MBC medium 0 out of 49 white/brown calli became green and produced shoots, whereas on MBC medium supplemented with 5 $\mu$M 17-β-estradiol, 13 out of 65 white/brown calli became green and produced shoots. This experiment used the same number of root explants with inducer as without inducer. Since 65 calli formed with inducer and only 49 without inducer, overexpression of CKI1 may also increase the efficiency of callus formation.

EXAMPLE 15

Transfection of Arabidopsis Roots with XVE-CKI1

A) Preparation of Root Material

Freshly harvested seeds are stored dry at 4° C. for two weeks before use. Seeds are sterilized by placing them into a 1.5 mL Eppendorf tube (or other convenient container) with about 1 mL of sterilization solution (50% Clorox+ 0.01% Triton X-100) and agitating regularly for 10 minutes. It is best not to use too many seeds (>1000 or about 50 $\mu$L) in a 1.5 mL Eppendorf tube because using too large a number of seeds results in inefficient sterilization. The sterilization solution is removed with a sterile pipette and the seeds are washed three times in sterile distilled water using 1.0–1.5 mL for each rinse.

The sterilized seeds are suspended in about 0.5 mL of a sterile 0.15% agar in water solution and then spread onto the surface of A plates (MS salts+30 g/L sucrose+0.8 g/L agar, pH 5.7). The seeds are vernalized at 4° C. for two days to improve seed germination frequency. The seeds are then incubated in a culture room and germinate in three days. One week seedlings are used for root culture.

Ten to 15 seedlings are transferred to a 250 mL Erlenmeyer flask containing 100 mL B5 medium (B5 salts+30 g/L sucrose+0.5 g/L MES (2-[N-morpholino]ethanesulfonic acid), pH 5.7). The flask is loosely sealed with two layers of aluminum foil and placed on a shaker set at 125 rpm. Cultures are illuminated with dim light at 22° C. After 10–15 days in culture in B5 medium, the roots are used for transformation. White roots should be selected for transformation. Yellow or slightly brownish roots cannot be transformed well.

B) Pretreatment of Root Explants

The following steps should be performed in a sterile hood. Roots prepared as in step (A) are transferred to a sterile Petri dish. A sterile scalpel is used to cut off the root system from the plantlets. The roots are cut into approximately 1 cm segments and placed onto a sterile paper towel to blot up excess medium. The root segments are then transferred onto F1 plates (B5 salts+20 g/L glucose+0.5 g/L MES+0.5 mg/L 2,4-D+0.05 mg/L Kinetin+2 g/L phytagel, pH 5.7) using sterile forceps. The roots are spread out so that they are all in contact with the medium. The plates are sealed with gas-permeable tape and are incubated in a tissue culture room for 2–3 days.

C) Growth of Agrobacterium

Agrobacteria (strain LBA4404; Clontech) were transformed with constructs pER8-CKI1 (XVE-CKI1), and the resulting transformants were cultured in YEB medium (5 g/L sucrose, 5 g/L peptone, 5 g/L beef extracts and 1 g/L yeast extracts, 0.04 g/L MgSO$_4$7H$_2$O, pH 7.0) supplemented with 100 mg/L spectinomycin and 100 mg/L streptomycin overnight at 28° C. The Agrobacteria were then pelleted and washed twice with YEB medium without antibiotics, and finally suspended in 2.0–2.5 mL YEB for infection of Arabidopsis root explants.

D) Inoculation of Root Explants with Agrobacterium and Cocultivation

The root explants prepared as in part B above are transferred to a sterile Petri dish and cut into 0.5 cm segments. The root explants are transferred to a sterile basket (e.g., a glass tube with a mesh cover on one end) which is put into a Petri dish which contains 20 mL B5 medium. 2 mL of Agrobacterium solution from step C are placed into the B5 medium. The basket is swirled gently for about 2 minutes to be certain that the root explants are inoculated with Agrobacterium. After inoculation, the basket which contains the root explants is placed on 4 layers of sterile paper towels to blot up excess liquid. Clumps of root segments are removed a few at a time from the basket using forceps and are placed onto F2 plates (F1 plates +20 mg/L acetosyringone) in clumps of 5–10 root segments. The root segments are cocultivated with Agrobacteria for 2–3 days at 22° C.

E) Selection and Regeneration of Transformants

After cocultivation of root segments with Agrobacteria, the Agrobacteria are washed away from the root explants by using sterile distilled water containing 200 mg/L carbenicillin. The root explants are collected in a basket which is then placed onto sterile paper towels to blot up excess liquid. The root segments are transferred to MIC medium (MS salts+10 g/L sucrose+0.5 g/L MES+0.15 mg/L indole acetic acid (IAA)+100 mg/L carbenicillin+2.0 g/L phytagel, pH 5.7) with or without a chemical inducer (5 μM 17-β-estradiol) and cultured at 22° C. for a cycle of 16 hours of white light and 8 hours of dark. The MIC medium contains MS salts, IAA and carbenicillin but does not contain the antibiotics for the selection of transformants. It is noted that the presence of IAA is not critical but does increase the efficiency of regeneration when used with Arabidopsis. IAA has a negative effect when used with tobacco.

The above is subcultured to the same medium after the first week and then subcultured every two weeks. After about 10 days of culture, a small dark green callus appears on the explants which are grown on medium with the chemical inducer, but no green callus appears on the plate without the chemical inducer. After about 15 days, small shoots appear on the medium with the chemical inducer. After the shoots form small rosettes (3–4 leaves), they are transferred to MIC medium without the chemical inducer to promote root regeneration. After root regeneration, the plantlets are transferred to soil and grown to maturity. When transferring the plantlets to soil, the agar medium should be washed clearly away from the plantlets. During the first two days in soil the plantlets should be covered with a plastic wrap to maintain high moisture.

F) Maturation of Transgenic Plants

After about 5–6 weeks, most siliques become yellow and dry. Seeds are collected individually and stored at 4° C.

EXAMPLE 16

Transfection of Arabidopsis with XVE-Lec1

Overexpression of Lec1 under the control of the XVE inducible system (pER8-Lec1) leads to the formation of somatic embryos or embryo-like structures in the cotyledons in transgenic Arabidopsis seedlings. This system can be used to produce somatic embryos under plant hormone-free conditions in the absence of any plant hormones. This differs from all current tissue culture methods in which formation of somatic embryos is dependent on 2,4-D. After transfer onto medium without the inducer, the somatic embryos will germinate into seedlings, thereby producing transformants which do not express an antibiotic selectable marker. Conditional overexpression of Lec1 can also increase the efficiencies of transformation and regeneration for monocots and gymnosperms. Using prior art techniques, it has been very difficult to obtain regenerants and/or transformants for most economically important species. This method is particularly important for monocots and gymnosperms, whose regeneration is mainly through the somatic embryogenesis pathway.

EXAMPLE 17

Transfection with XVE-SERK

The Arabidopsis SERK gene was cloned by PCR (polymerase chain reaction). The SERK gene was placed under the control of the XVE system. The XVE-SERK construct was used to transfect tobacco and Arabidopsis. Upon induction, somatic embryos will form under plant hormone-free conditions in the absence of any added plant hormones. Prior art techniques required the presence of 2,4-D for formation of somatic embryos. After transfer to medium without the inducer, the somatic embryos will germinate into seedlings, thereby producing transformants which do not express an antibiotic selectable marker. Conditional overexpression of SERK will also increase efficiencies of transformation and regeneration for monocots and gymnosperms, which previously have been very difficult to regenerate and/or transform. This method is particularly important for monocots and gymnosperms whose regeneration is mainly through the somatic embryogenesis pathway.

EXAMPLE 18

Dual-inducible Systems

A major goal is to develop a double inducible expression system in which multiple genes can be independently and inducibly regulated. Transgenic Arabidopsis plants carrying a) XVE and b) GVG can be generated by cotransformation or crosses between individual lines. Each component in the dual-inducible system will operate independently and will not interfere with one another and they will maintain their inducibility and tight control. Genes under the control of each promoter can be induced in either order or simultaneously by proper use and timing of inducer.

EXAMPLE 19

Use of a Knotted Gene to Induce Shoot Formation

The knotted1 gene and its family members, e.g., the knotted1 homologous genes KNAT1 and KNAT2, are highly expressed in shoots (Lincoln et al., 1994; Chuck et al., 1996). Transgenic plants which have been transformed with, e.g., the KNAT1 gene under the control of a CaMV 35S promoter have severe alterations including ectopic shoot formation (Lincoln et al., 1994). However, such shoots are unable to develop normally because of the uncontrolled expression of the knotted gene. A system in which plants are transformed with knotted genes which are regulatable will allow one to produce plants which will produce shoots and then to use the shoots to regenerate normal plants by shutting off the expression of the gene in the shoots. The present invention is one method of accomplishing such a result. A knotted gene, e.g., kn1 from maize, is placed in a vector such that it is under the control of the GVG system described above. Plants which have been transformed with this vector will grow normally in the absence of an inducer of the GVG or XVE system. Explants, e.g., leaf disks, of these transgenic plants can be treated with an inducer (e.g., dexamethasone or 17-β-estradiol) to stimulate the development of adventitious shoots. The developed shoots can be excised and transferred to a medium without the inducer. These shoots will then develop normally to yield transgenic plants. The vectors used may include other genes of interest, which are not under the control of the GVG or XVE system, which it is desired to transform into the plants. The selected plants will include the gene of interest and will have been selected without the requirement of using an antibiotic selectable marker. Note that the selection for transformed shoots should be performed as in Example 3, i.e., on medium without hormones (MBC) but with carbenicillin to kill Agrobactera. Homologs of the maize knotted gene from other monocot or dicot plants may be used for the same purpose.

EXAMPLE 20

Use of a CKI1 Gene to Induce Shoot Formation

The gene CKI1 was recently identified (Kakimoto, 1996). Overproduction of this gene in plants results in plants which exhibit typical cytokinin responses, including rapid cell division and shoot formation in tissue culture in the absence of exogenous cytokinin (Kakimoto, 1996). The CKI1 gene can be used as a selectable marker in a manner similar to ipt. A system in which plants are transformed with CKI1 which is regulatable will allow one to produce plants which will produce shoots and then to use the shoots to regenerate normal plants by shutting off the expression of the gene in the shoots. The present invention is one method of accomplishing such a result. A CKI1 gene is placed in a vector such that it is under the control of the GVG system described above. Plants which have been transformed with this vector will grow normally in the absence of an inducer of the GVG system. Explants, e.g., leaf disks, of these transgenic plants can be treated with an inducer (e.g., dexamethasone) to stimulate the development of adventitious shoots. The developed shoots can be excised and transferred to a medium without the inducer. These shoots will then develop normally to yield transgenic plants. The vectors used may include other genes of interest, which are not under the control of the GVG system, which it is desired to transform into the plants. The selected plants will include the gene of interest and will have been selected without the requirement of using an antibiotic selectable marker. As in Examples 3 and 19, the selection is performed on MBC plates for shoots which are then transferred to MBCI for rooting.

EXAMPLE 21

Vectors with Antibiotic Resistance or

Herbicide Resistance Genes Under GVG or XVE Control

Antibiotic resistance causing genes have been widely used in vectors as selectable markers. One problem with such systems is that these genes tend to be constitutively active and the transformed plants which are obtained will continue to express these genes. There have been environmental and health concerns over inserting such constitutively expressed genes into plants which are grown outside of a laboratory setting (Bryant and Leather, 1992; Gressel, 1992; Flavell et al., 1992). Placing such genes under the control of the GVG or XVE system overcomes these drawbacks. The antibiotic resistance genes will be expressed only during the selection process at the time when a glucocorticoid is present in the growth medium, but the genes will not be activated when grown outside of the laboratory in the absence of glucocorticoid. Any desired antibiotic resistance gene may be utilized. Appropriately modified pTA7001 and pTA7002 vectors can be utilized for this purpose. The antibiotic gene of interest is cloned into, e.g., the XhoI-SpeI cloning site. The pTA7001 or pTA7002 vectors will be modified such that the hpt gene is inactivated or removed. These modified vectors may be used. Suitable vectors can be prepared by starting with, e.g., the pBI101 (Clontech) vector. The region between the left and right borders of the vector is removed and replaced with the GVG or XVE system described above which includes, in brief, the 35S promoter, the GAL4 DNA binding domain, the VP16 transactivating domain, and the glucocorticoid receptor domain plus the 6×GAL4 UAS region followed by a cloning site. Such vectors do not include an endogenous antibiotic resistance gene. Any desired antibiotic gene can be inserted into the cloning site near the 6×GAL4 UAS region and will be under the control of the glucocorticoid. The hygromycin phosphotransferase gene and the neomycin phosphotransferase (npt) gene are two examples of antibiotic genes which may be utilized. Ti-vectors which include a DEX regulatable npt or hpt gene can be used to transform explants of the desired species. During the tissue culture phase, regenerated shoots will be selected in the presence of DEX (which activates the appropriate antibiotic resistance gene) and in the presence of the appropriate antibiotic (kanamycin or hygromycin). Once verified, transgenic shoots can then be transferred into tissue culture medium with the antibiotic but without the chemical inducer (DEX). The resulting plants will contain the antibiotic resistance genes but these genes will not be active in the absence of a chemical inducer.

Herbicide resistance genes can be similarly placed under GVG or XVE control and used for selection of transformed plants during tissue culture phase. Such plants would not express the herbicide resistance genes in the field. Examples of herbicide resistant genes are PAT (phosphinothricin acetyltransferase) which confers resistance to the BASTA herbicide (active ingredient phosphinothricin) (Rathore et al., 1993; Becker et al., 1992) and a mutant form of acetolactate synthase which is resistant to a sulfonylurea herbicide of DuPont (see, e.g., Wiersma et al., 1989; Harms et al., 1992; Hattori et al., 1992; Hattori et al., 1995). In theory these genes could be used not only as selectable markers in tissue culture but could also be expressed in the field. Because of the possible dangers of spraying DEX or 17-β-estradiol one would not want to spray DEX onto plants in a field, but this method could be used if a safer compound than DEX is used as an inducer.

EXAMPLE 22

Plant Growth and Transformation

*Nicotiana tabacum* seeds cultivar SR1 were surface sterilized in 30% commercial bleach containing 0.02% Tween 20 for 10 minutes and washed five times with sterile water. Plants were grown in a tissue culture room at 22° C. at 16 hour light and 8 hour dark cycles. Tobacco transformation was essentially as described by Horsch et al. (1985) and Klee et al. (1987). Leaf discs were prepared from young leaves of four week old plants and the explants were cultured for two days on MB medium (MS salts, B5 vitamins, 20 g/L sucrose, 20 mg/L acetosyringone, 0.2% phytagel, pH 5.7). After a three-day co-cultivation with *Agrobacterium tumefaciens* the leaf discs were transferred to MS medium containing different DEX concentrations. After 20 to 40 days of culturing, regenerated shoots were excised from explants and cultured on MS medium containing IAA to induce root regeneration.

Sterilized lettuce leaves (*Lactuca sativa* var. Great Lake #118) were germinated and the seedlings were grown as described for tobacco. Transformation of lettuce leaf discs was performed as described by Curtis et al. (1996) with the exception that cytokinin was omitted from the culture media.

EXAMPLE 23

Optimization of the Conditions for the Induction of the ipt Gene in Transformed Cells Tobacco leaf discs and lettuce leaf disks, obtained from transfection with pTA7002G/ipt/luc, were placed on media containing carbenicillin and different concentrations of dexamethasone (DEX). The explants were transferred to fresh medium every two weeks to maintain constant culture conditions. The number of shoots that were regenerated from a given number of leaf discs increased dramatically as the concentration of DEX increased (Table 2). One hundred seventy tobacco shoots and 198 lettuce shoots were regenerated from 28 explants at 10 μM DEX. In the absence of DEX, only 7 shoots were regenerated in tobacco and 30 shoots regenerated in lettuce from 28 explants each (FIG. 8).

TABLE 2

|  | Tobacco | | | | Lettuce | |
|---|---|---|---|---|---|---|
| DEX (μM) | 0 | 0.1 | 1 | 10 | 0 | 10 |
| Total number of regenerants per 28 explants | 7 | 139 | 129 | 170 | 30 | 198 |
| Number of examined regenerants | 7 | 72 | 72 | 72 | 28 | 28 |
| Percentage of LUC$^+$ regenerants | 42 | 29 | 44 | 49 | 12 | 46 |

EXAMPLE 24

Measurement of Luc Activity in Tobacco and Lettuce Regenerants

The transformation cassette pTA7002G/ipt/luc (FIG. 12) contained a luc gene under the control of the CaMV 35S promoter (Millar et al., 1992; Benfey and Chua, 1990). Luc activity was measured in order to estimate the number of transgenic shoots using the video imaging is system described by Michelet and Chua (1996). Measurements were integrated over 5 minutes and the corresponding background was subtracted from the images (FIGS. 9A–F). Approximately 50% of the regenerants expressed the luc gene (Table 2). Under non-inductive conditions (0 μM DEX) 42% of the tobacco regenerants and 12% of the lettuce regenerants showed detectable Luc activity (Table 2). This indicates that a small percentage of the transformed cells were very sensitive towards cytokinin whose levels might be slightly elevated due to leaky ipt expression. Because of the high yield of regenerants the experiments described below were performed using shoots from explants that were treated with 10 μM DEX.

EXAMPLE 25

Measurement of the Effect of Induction of ipt with DEX Over Time

To further characterize the transformation system, we examined the effects of the duration of induction as well as the effects of exogenously applied phytohormones. Time course experiments were performed to determine whether the specificity of the induction of the ipt gene decreases over time due to overproduction and diffusion of cytokinin, which could trigger regeneration events in neighboring, non-transformed cells. The Luc activity in 54 tobacco regenerants (obtained from a transfection with pTA7002G/ipt/luc) was measured after 20, 30, and 40 days of induction with 10 μM DEX to estimate the transformation frequency. No significant difference in the percentage of regenerants with detectable Luc activity was found over time. After 20 days, 46% of regenerants had detectable Luc activity and after both 30 and 40 days 53% of regenerants had detectable Luc activity. In addition, there were no detectable changes in the transformation efficiency (determined as Luc activity) when ipt gene expression was directly induced during the co-cultivation period with Agrobacterium. Similar results have been obtained with lettuce.

EXAMPLE 26

Influence of Exogenously Applied Auxin During Induction

Luciferase activity was measured in shoots from tobacco explants (obtained from a transfection with pTA7002G/ipt/luc) that were cultured for 40 days on medium containing 1.0, 1.5, and 2.0 mg/mL auxin and 10 μM DEX. High auxin to cytokinin levels favored root regeneration and had a suppressing effect on shoot regeneration, and therefore, might reduce the number of non-transgenic regenerants. No significant difference in luciferase activity occurred at different auxin concentrations. At 1.0 mg/mL auxin 45% of regenerants had detectable Luc activity, at 1.5 mg/mL auxin 58% of regenerants had detectable Luc activity, and at 2.0 mg/mL auxin 47% of regenerants had detectable Luc activity.

EXAMPLE 27

Determination of ipt Transcript Levels in Shoots Using Northern Analysis

The level of ipt transcripts was determined in 30 day-old tobacco and lettuce regenerants (from a transfection with pTA7002G/ipt/luc) with and without detectable luciferase activity. The regenerants were grown in the presence of 10 μM dexamethasone.

RNA was extracted from 0.1 g of plant material using Qiagen RNA extraction kits and protocols. Total RNA was separated on 1% agarose gels containing 0.8 M formaldehyde. RNA was transferred to Duralon UV membranes according to the manufacturer's instructions (Stratagene). After blotting, the RNA was covalently cross-linked to the membrane by UV irradiation. The membranes were blocked and hybridization was performed using Stratagene QuikHyb® solution at 68° C. according to the manufacturer's instructions. After hybridization the membranes were washed three times for 15 minutes with 2×SCC+0.1% SDS at 65° C. and once with 0.1×SSC+0.1% SDS at 60° C. for 15 minutes.

The results of Northern analysis revealed that with only one exception (FIG. 10C, sample f) all tested tobacco and lettuce regenerants expressed ipt transcripts (Table 3). The amount of ipt transcript was higher in tobacco than in lettuce regenerants and varied between different shoots. Transcript levels for ipt were higher in LUC+ shoots than in regenerants without detectable luciferase activity (LUC−). This indicates that regeneration was almost totally coupled to ipt gene expression leading to elevated cytokinin levels.

TABLE 3

| Number of tobacco regenerants | Luciferase activity | ipt transcript | luc transcript | luc (copy number) |
|---|---|---|---|---|
| 9 | + | + | + | 1 |
| 1 | + | + | + | >1 |
| 3 | − | + | shorter | 1 |
| 1 | − | + | shorter | >1 |
| 3 | − | + | − | 0 |
| 1 | − | − | − | 0 |

EXAMPLE 28

Determination of the Presence of the luc Gene and the Level of Its Transcript in Shoots Using Southern and Northern Analysis To assay the presence of the luc gene, Southern blot analysis was performed using DNA from LUC+ and LUC− tobacco regenerants (obtained from transfection with pTA7002G/ipt/luc). DNA was extracted from 0.1 g tobacco plant material using Nucleon DNA extraction kits and protocols. DNA was separated on 0.8% agarose gels. DNA was transferred to Duralon UV membranes according to the manufacturer's instructions (Stratagene). After blotting, the DNA was covalently cross-linked to the membrane by UV irradiation. The membranes were blocked and hybridized using Stratagene QuikHyb® solution at 68° C. according to the manufacturer's instructions. After hybridization the membranes were washed three times for 15 minutes with 2×SSC+0.1% SDS at 65° C. and once with 0.1×SSC+0.1% SDS at 65° C. for 15 minutes. The luc gene was found in all LUC+ regenerants and in 50% of the LUC− shoots.

Northern analysis was performed according to Example 27 in order to assay the presence of luc transcripts in LUC+ and LUC− tobacco regenerants. LUC− regenerants possessed smaller, less abundant luc transcripts compared to the luc transcripts from LUC+ regenerants, which were larger and more abundant (Table 3).

EXAMPLE 29

Analysis of Hygromycin Resistance

Expression of the hpt gene confers hygromycin resistance. To assay the presence of the hpt gene in LUC+ and LUC− tobacco regenerants (obtained by transfection with pTA7002G/ipt/luc), hygromycin resistance was assayed as discussed in Example 3. Young leaf blades with petiole were placed into an agar medium with hygromycin and scored for root formation. Hygromycin resistance was tested on plates with non-inductive medium containing 20 mg/L hygromycin. Ninety-five percent of all tested LUC+ tobacco regenerants were resistant to hygromycin and more than 60% of the tested LUC− shoots were hygromycin-resistant.

EXAMPLE 30

Root Regeneration, Plant Morphology, and Copy Number in Tobacco

Tobacco shoots (obtained from transfection with pTA7002G/ipt/luc) were transferred to a root-inducing medium (1×MS salts, B5 vitamins, 0.15 mg/L IAA, 20 g/L sucrose, 0.2% phytagel, pH 5.7) that did not contain DEX. Over 40% of the transgenic tobacco shoots developed a strong root system within 20 days after transfer. With very few exceptions (less than 2%) the morphology of the transgenic tobacco plants appeared normal. The tobacco plants were then transferred to soil. The plants developed normal leaves and flowers and were apparently unaffected in seed production.

Segregation analysis for the luc gene family was performed with 44 randomly selected seedlings (T1 progeny) of one transgenic tobacco line (FIGS. 11A–B). Seeds were taken from transgenic plants that had been self-crossed. A population of the progeny (germinated plantlets) were analyzed. Luciferase activity measurements in these seedlings showed a clear 3:1 segregation of the dominant luc gene. This showed an insertion into one locus and that the transgene was stably transmitted into the second generation.

Southern analysis was performed with DNA from the seedlings after digestion of the DNA with restriction enzymes. Single gel bands were detected (FIG. 11C).

EXAMPLE 31

Southern Blot Analysis of Tobacco Regenerants

Southern analysis was performed with DNA from eighteen tobacco regenerants (obtained from transfection with pTA7002G/ipt/luc) after digestion with BamHI, SacI, and XbaI. Most of the shoots contained only a single copy of the transgene. Only two out of eighteen regenerants showed the presence of more than one hybridizing band (Table 3).

While the invention has been disclosed herein by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

References

Ainley, W. M. and Key, J. L. (1990). *Plant Mol. Biol.* 14:949–966.

Akiyoshi, D. E., Klee, H, Amasino, R. M., Nester, E. W. and Gordon, M. P. (1984). *Proc. Natl. Acad. Sci. USA* 81:5994–5998.

Aoyara, T. and Chua, N.-H. (1997). *Plant J.* 11:605–612.

Aoyama, T., Dong, C.-H., Wu, Y., Carabelli, M. Sessa, G., Ruberti, I. Morelli, G. and Chua, N.-H. (1995). *Plant Cell* 7:1773–1785.

Barry, G. F., Rogers, S. G., Fraley, R. T. and Brand, L. (1984). *Proc. Natl. Acad. Sci. USA* 81:4776–4780.

Beato, M. (1989). *Cell* 56:335–344.

Beavan, M. W. and Chilton, M. D. (1982). *Annu. Rev. Genet.* 16:357–384.

Becker, D., Kemper, E., Schell, J. and Masterson, R. (1992). *Plant Molecular Biology* 20:1195–1197.

Benfey, P. N. and Chua, N.-H. (1990). *Science* 250:956–966.

Braselmann, S., Graninger, P. and Busslinger, M. (1993). *Proc. Nail. Acad. Sci. USA* 90:1657–1661.

Bryant, J. and Leather, S. (1992). *Trends Biotechnol.* 10:274–275.

Chaudhury, A. M., Letham, S., Craig, S. and Dennis, E. S. (1993). *Plant J.* 4:907–916.

Chuck, G., Lincoln, C. and Hake, S. (1996). *The Plant Cell* 8:1277–1289.

Cline, M. G. (1991). *Physiol. Plant.* 90:230–237.

Coenen, C. and Lomax, T. (1997). *Trends Plant Sci.* 2:351–355.

Coruzzi, G., Broglie, R., Edwards, C. and Chua, N.-H. (1984). *EMBO J.* 3:1671–1679.

Curtis, I. S., Power, J. B., Blackhall, N. W., de Laat, A. M. M. and Davey, M. R. (1996). *J. Exp. Bot.* 45:1441–1449.

Dalrymple, M. A., McGeoch, D. J., Davison, A. J. and Preston, C. M. (1985). *Nucl. Acids Res.* 13:7865–7879.

Davies, P. E. (ed.) (1995). *Plant Hormones and Their Role in Plant Growth and Development*, Kluwer Academic Publisher, Dordrecht.

de Wet, J. R., Wood, K. V., DeLuca, M., Helinski, D. R. and Subramani, S. (1987). *Mol. Cell. Biol.* 7:725–737.

Ebinuma, H., Sugita, K., Matsunaga, E. and Yamakado, M. (1997). *Proc. Natl. Acad. Sci. USA* 94:2117–2121.

Faiss, M., Zalubilova, Stmad, M. and Schmülling, T. (1 997). *Plant Journal* 12:401–415.

Flavell, R. B., Dart, E., Fuchs, R. L. and Fraley, R. B. (1992). *Bio/Technology* 10:141–144.

Fluhr, R., Moses, P., Morelli, G., Coruzzi, G. and Chua, N.-H. (1986). *EMBO J.* 5:2063–2071.

Gan, S. and Amasino, R. M. (1995). *Science* 270:1986–1988.

Gatz, C. (1996). *Curr. Opin. Biotechnol.* 7:168–172.

Gatz, C., Frohberg, C. and Wendenburg, R. (1992). *Plant J.* 2:397–404.

Giniger, E., Varnum, S. and Ptashne, M. (1985). *Cell* 40:767–774.

Goldberg, S. B., Flick, J. S. and Rogers, S. G. (1984). *Nucl. Acids. Res.* 12:4665–4677.

Goodrich, J. A., Hoey, T. Thut, C. J., Admon, A. and Tjian, R. (1993). *Cell* 75:519–530.

Greene, G. L., Gilna, P., Waterfield, M., Baker, A., Hort, Y. and Shine, J. (1986). *Science* 231:1150–1154.

Gressel, J. (1992). *Trends Biotechnol.* 10:382.

Harms, C. T., Armour, S. L., DiMaio, J. J., Middlesteadt, L. A., Murray, D., Negrotto, D. V., Thompson-Taylor, H., Weymann, K., Montoya, A. L., Shillito, R. D., et al. (1992). *Mol. Gen. Genet.* 233:427–435.

Hattori, J., Rutledge, R., Labbe, H., Brown, D., Sunohara, G. and Miki, B. (1992). *Mol. Gen. Genet.* 232:167–173.

Hattori, J., Brown, D., Mourad, G., Labbe, H., Ouellet, T., Sunohara, G., Rutledge, R., King, J. and Miki, B. (1995). *Mol. Gen. Genet.* 246:419–425.

Horii, T., Ogawa, T. and Ogawa, H. (1981). *Cell* 23:689–697.

Horsch, R. B., Frey, J. E., Hofman, N. L., Eichholtz, D. Rogers, S. G. and Fraley, R. J. (1985). *Science* 227:1229–1231.

Horsch, R., Fry, J., Hofman, N., Neidermeyer, J., Rogers, S. and Fraley, R. (1988). In *Plant Molecular Biology Manual*, A5 (Gelvin, S. and Schilperoort, R., eds). Dordrecht, The Netherlands: Kluwer Academic Publishers, pp. 1–23.

Ishige, F. Takaichi, M. Foster, R., Chua, N. H. and Oeda, K. (1999). *Plant J.* 18:443–448.

Kakimoto, T. (1996). *Science* 274:982–985.

Keegan, L., Gill, G. and Ptashne, M. (1986). *Science* 231:699–704.

Klee, H., Rorsch, R. and Rogers, S. (1987). *Ann. Rev. Plant Physiol.* 38:467–486.

Kost, B. Spielhofer, P. and Chua, N.-H. (1998). *Plant J.* 16:393–401.

Kunkel, T., Niu, W.-W., Chan, Y. S. and Chua, N.-H. (1999). *Nat. Biotechnol.* 17:916–919.

Kuraish, S. and Okumura, F. S. (1956). *Bot. Mag.* 69:817.

Laughon, A. and Gesteland, R. (1 984). *Mol. Cell. Biol.* 4:260–267.

Lin, Y.-S., Maldonado, E., Reinberg, D. and Green, M. R. (1991). *Nature* 353:569–571.

Lincoln, C., Long, J., Yamaguchi, J., Serikawa, K. and Hake, S. (1994). *The Plant Cell* 6:1859–1876.

Lloyd, A. M., Schena, M., Walbot, V. and Davis, R. W. (1994). *Science* 266:436–439.

Louvion, J.-F., Havaux-Copf, B. and Picard, D. (1993). *Gene* 131:129–134.

McKenzie, M. J., Mett, V., Reynolds, P. H. S., and Jameson, P. E. (1998). *Plant Physiol.* 116:969–977.

Medford, J. I., Horgan, B. R., El-Sawi, Z., and Klee H. J. (1989). *Plant Cell* 1:403–413.

Mett, V. L., Lockhead, L. P. and Reynolds, P. H. S. (1993). *Proc. Natl. Acad. Sci. USA* 90:4567–4571.

Michelet, B. and Chua, N.-H. (1996). *Plant Mol. Biol. Rep.* 14:320–329.

Miesfeld, R., Rusconi, S., Godowski, P. J., Maler, B. A., Okret, S., Widstroem, A.-C., Gustafsson, J.-A. and Yamamoto, K. R. (1986). *Cell* 46:389–399.

Miki, T., Ebina, Y., Kishi, F. and Nakazawa, A. (1981). *Nucleic Acids Res.* 9:529–543.

Miklashevichs, E. and Walden, R. (1997). *Physiologia Plant.* 100:528–533.

Millar, A. J., Short, S. R., Chua, N.-H., and Key, S. A. (1992). *Plant Cell* 4:1075–1087.

Mok, D. W. S. and Mok, M. C. (1994). *Cytokinins: Chemistry Activity and Function* (Mok, D. W. S. and Mok, M. C., eds.) Boca Raton, Fla.: CRC Press.

Murashige, T. and Skoog, F. (1962). *Physiol. Plant.* 15:493–497.

Nagy, F., Kay, S. A. and Chua, N.-H. (1988). In *Plant Molecular Biology Manual*, B4 (Gelvin, S. and Schilperoort, R., eds). Dordrecht, The Netherlands: Kluwer Academic Publishers, pp. 1–12.

Odell, J. T., Nagy, F. and Chua, N.-H. (1 985). *Nature* 313:810–812.

Ooms, G., Kaup, A. and Roberts, J. (1983). *Theor. Appl. Genet.* 66:169–172.

Picard, D. (1993). *Trends Cell Biol.* 3:278–280.

Picard, D., Salser, S. J. and Yamamoto, K. R. (1988). *Cell* 54:1073–1080.

Rathore, K. S., Chowdhury, V. K. and Hodges, T. K. (1993). *Plant Molecular Biology* 21:871–884.

Redig, P., Schmülling, T., and Van Onckelen, H. (1996). *Plant Physiol.* 112:141–148. Rusconi, S. and Yamamoto, K. R. (1987). *EMBO J.* 6:1309–1315.

Sachs, T. and Thimmann, K. V. (1967). *Am. J. Bot.* 54:136–144.

Sadowski, I., Ma, J., Triezenberg, S. and Ptashne, M. (1988). *Nature* 335:563–564.

Schena, M., Lloyd, A. M. and Davis, R. W. (1991). *Proc. Natl. Acad. Sci. USA* 88:10421–10425.

Skoog, F. and Miller, C. O. (1 957). *Symp. Soc. Expl. Biol.* 11:118–131.

Smigocki, A. C. and Owens, L. D. (1988). *Proc. Natl. Acad. Sci. USA* 85:5131–5135.

Smigocki, A. C. and Owens, L. D. (1989). *Plant Physiol.* 91:808–811.

Thompson, J. F., Hayes, L. S. and Lloyd, D. B. (1991). *Gene* 103:171–177.

Tran Thanh Van, K. M. (1981). *Ann. Rev. Plant Physiol.* 32:292–311.

Triezenberg, S. J. Kingsbury, R. C. and McKnight, S. L. (1988). *Genes Devel.* 2:718–729.

Valvekens, D., Van Montagu, M. and Van Lijsebettens, M. (1988). *Proc. Natl. Acad Sci. USA* 85:5536–5540.

Waldron, C., Murphy, E. B., Roberts, J. L., Gustafson, G. D., Armour, S. L. and Malcom, S. K. (1985). *Plant Mol. Biol.* 5:103–108.

Weinmann, P., Gossen, M., Hillen, W., Bujard, H. and Gatz, C. (1994). *Plant J.* 5:559–569.

Wiersma, P. A., Schmiemann, M. G., Condie, J. A., Crosby, W. L. and Moloney, M. M. (1989). *Mol. Gen. Genet.* 219:413–420.

Wingler, A., von Schaewen, A., Leegood, R. C., Lea, P. J. and Quick, W. P. (1998). *Plant Physiol.* 116:329–335.

Yoder, J. I. and Goldsbrough, A. P. (1994). *Bio/Technology* 12:263–267.

4. The vector of claim 2 wherein said gene is a gene for antibiotic resistance.

5. The vector of claim 2 wherein said gene is a gene for herbicide resistance.

6. The vector of claim 1 wherein said vector further comprises one or more genes of interest.

7. The vector of claim 1, further comprising a luciferase gene.

8. The vector of claim 1 wherein said promoter is a constitutive promoter.

9. The vector of claim 8 wherein said constitutive promoter is G1090.

10. The vector of claim 1 wherein said promoter is a tissue-specific promoter.

11. An isolated nucleic acid encoding a transcription factor, comprising, in the 5' to 3' direction, i) a promoter, ii) DNA encoding a DNA binding domain of the bacterial repressor LexA, iii) DNA encoding a transactivating domain

---

---

What is claimed is:

1. A vector comprising a DNA sequence encoding a transcription factor, having the following elements in the 5' to 3' direction, i) a promoter, ii) DNA encoding a DNA binding domain of the bacterial repressor LexA, iii) DNA encoding a transactivating domain of VP16, iv) DNA encoding the regulatory domain of an estrogen receptor.

2. The vector of claim 1 wherein said vector further comprises a gene encoding a selectable marker, the expression of which is controlled by the transcription factor.

3. The vector of claim 2 wherein said gene is isopentenyltransferase (ipt), cytokinin-independent 1 (CKI1), luciferase, a member of the knotted family, a gene the expression of which can promote shoot regeneration and development, or a gene the expression of which promotes somatic embryogenesis.

of VP16, iv) DNA encoding a regulatory domain of an estrogen receptor.

12. A transgenic plant or transgenic plant cell comprising the nucleic acid of claim 11.

13. The transgenic plant or transgenic plant cell of claim 12, further comprising a gene encoding a selectable marker the expression of which is controlled by the transcription factor.

14. The transgenic plant or transgenic plant cell of claim 13, wherein the gene is selected from the group consisting of isopententyltransferase (ipt), cytokinin-independent 1 (CKI1), a member of the knotted family, a gene the expression of which can promote shoot regeneration and development, or a gene the expression of which promotes somatic embryogenesis.

15. The transgenic plant or transgenic plant cell of claim 12, further comprising a luciferase gene.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Saccharomyces cerevisiae

<400> SEQUENCE: 1
cgggtgacag ccctccg                                           17

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:This is a
      G-box.

<400> SEQUENCE: 2
gccacgtgcc                                                   10